US012023373B2

United States Patent
Clemmensen et al.

(10) Patent No.: US 12,023,373 B2
(45) Date of Patent: Jul. 2, 2024

(54) GLYCO-ENGINEERED IMMUNIZATION ANTIGENS

(71) Applicant: EXPRES2ION BIOTECHNOLOGIES APS, Hørsholm (DK)

(72) Inventors: Stine Broch Clemmensen, Hørsholm (DK); Teit Max Moscote Søgaard, Kokkedal (DK); Willem Adriaan De Jongh, Holte (DK)

(73) Assignee: EXPRES2ION BIOTECHNOLOGIES APS, Hørsholm (DK)

( * ) Notice: Subject to any disclaimer, the term of this patent is extended or adjusted under 35 U.S.C. 154(b) by 35 days.

(21) Appl. No.: 17/421,898

(22) PCT Filed: Jan. 10, 2020

(86) PCT No.: PCT/EP2020/050591
§ 371 (c)(1),
(2) Date: Jul. 9, 2021

(87) PCT Pub. No.: WO2020/144358
PCT Pub. Date: Jul. 16, 2020

(65) Prior Publication Data
US 2022/0111027 A1    Apr. 14, 2022

(30) Foreign Application Priority Data
Jan. 10, 2019  (EP) ..................... 19151218

(51) Int. Cl.
| | |
|---|---|
| *A61K 39/00* | (2006.01) |
| *A61K 38/17* | (2006.01) |
| *A61K 39/39* | (2006.01) |
| *A61P 31/14* | (2006.01) |
| *C07K 14/71* | (2006.01) |
| *C12N 9/10* | (2006.01) |
| *C12N 15/81* | (2006.01) |
| *C12N 15/85* | (2006.01) |
| *C12P 21/00* | (2006.01) |

(52) U.S. Cl.
CPC .. *A61K 39/001106* (2018.08); *A61K 38/1741* (2013.01); *A61K 39/39* (2013.01); *A61P 31/14* (2018.01); *C07K 14/71* (2013.01); *C12N 9/1051* (2013.01); *C12N 15/815* (2013.01); *C12N 15/85* (2013.01); *C12P 21/005* (2013.01); *C12Y 204/01152* (2013.01); *A61K 2039/5258* (2013.01); *C12Y 204/01065* (2013.01)

(58) Field of Classification Search
CPC .. A61K 38/1741; C12N 15/815; C12N 15/85; C12P 21/005; C12Y 204/01065; C12Y 204/01152
See application file for complete search history.

(56) References Cited

U.S. PATENT DOCUMENTS 6,461,835 B1 * 10/2002 Cummings .......... C12N 9/1051
435/6.16
2006/0286637 A1    12/2006 Hamilton

FOREIGN PATENT DOCUMENTS

| EP | 2 090 648 A1 | 8/2009 |
| EP | 3 315 610 A1 | 5/2018 |

OTHER PUBLICATIONS

Lowe et al. The Journal of Biological Chemistry, 1991, vol. 266, No. 26, pp. 17467-17477.*
Kumura et al. BIOCHEMICALANDBIOPHYSICAL-RESEARCHCOMMUNICATIONS vol. 237, pp. 131-137, (1997).*
Leiter et al. JBC 1999, vol. 274, Issue 31, pp. 21830-21839.*
Munster et al. Journal of Biotechnology, 2006, vol. 121, Issue 4, pp. 448-457.*
Bai, S., et al., "A Guide to Rational Dosing of Monoclonal Antibodies," *Clin Pharmacokinet*, 2012, vol. 51(2), pp. 119-135.
Faye, L., et al., "Affinity Purification of Antibodies Specific for Asn-Linked Glycans Containing αl → 3 Fucose or β1 → 2 Xylose," *Analytical Biochemistry*, 1993, vol. 209, pp. 104-108.
Grav, L., et al., "One-step generation of triple knockout CHO cell lines using CRISPR/Cas9 and fluorescent enrichment," *Biotechnol. J.*, 2015, vol. 10, pp. 1446-1456.
Hjerrild, K., et al., "Production of full length soluble *Plasmodium falciparum* RH5 protein vaccine using a *Drosophila melanogaster* Schneider 2 stable cell line system," *Scientific Reports*, 2016, vol. 6, pp. 1-15.
Holmes, K., et al., "Assembly Pathway of Hepatitis B Core Virus-like Particles from Genetically Fused Dimers," *The Journal of Biological Chemistry*, 2015, vol. 290(26), pp. 16238-16245.
Khan, A., et al., "Humanizing glycosylation pathways in eukaryotic expression systems," *World J Microbiol Biotechnol*, 2017, vol. 33(4), pp. 1-12.
Kim, Y., et al., "Expression of β-1,4-galactosyltransferase and suppression of β-N-acetyolglucosaminidase to aid synthesis of complex N-glycans in insect *Drosophila* S2 cells," *Journal of Biotechnology*, 2011, vol. 1543, pp. 145-152.

(Continued)

*Primary Examiner* — Bao Q Li

(74) *Attorney, Agent, or Firm* — Womble Bond Dickinson (US) LLP

(57) ABSTRACT

Disclosed are immunization antigens that have been glyco-engineered to include non-native glycosylation patterns with a view to enhance their properties as antigens for use in such areas as vaccination and antibody production. Also disclosed are to means and methods for producing the glycomodified antigens as well of methods and uses of the glycomodified antigens.

Figure 1:
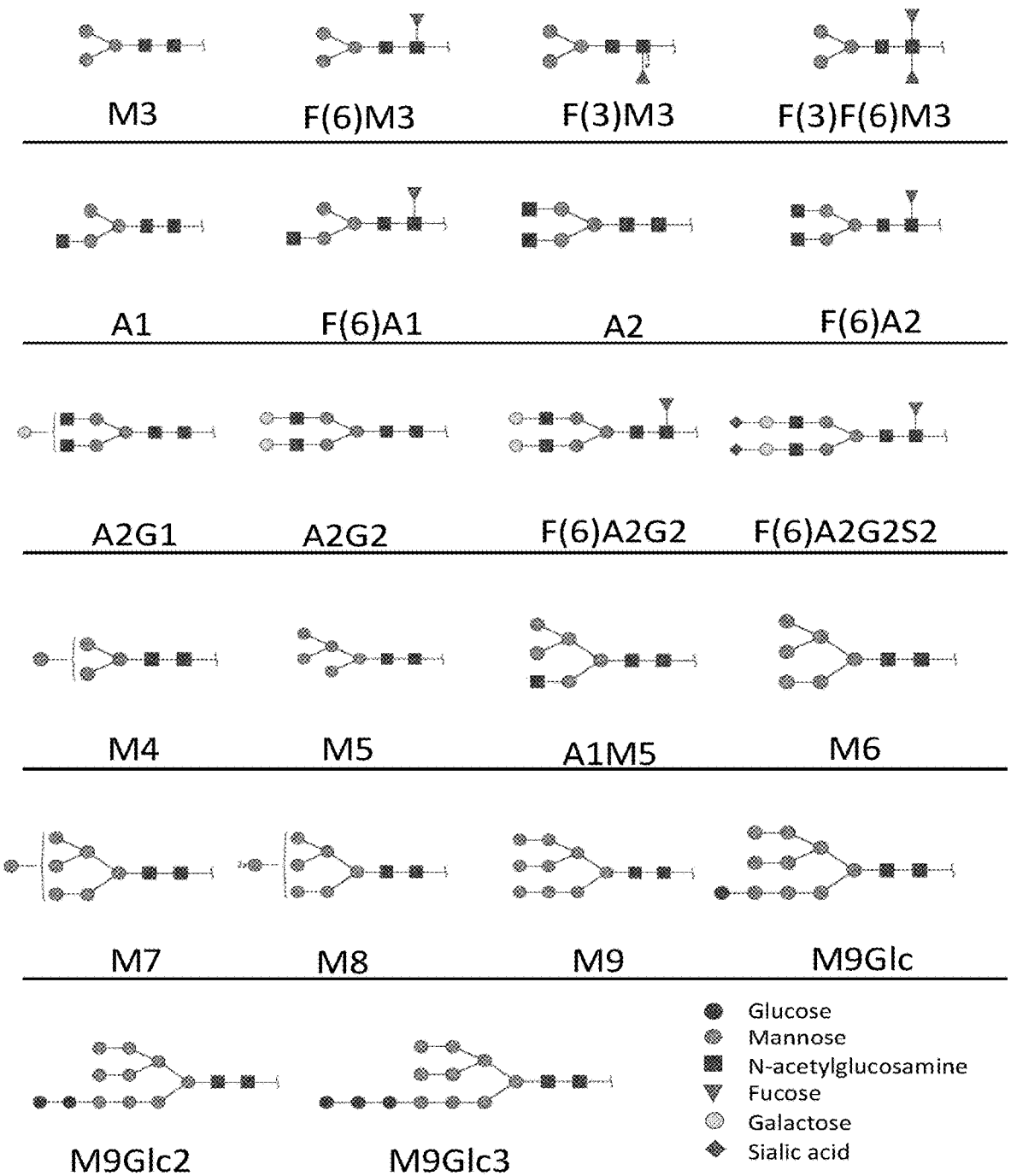

16 Claims, 13 Drawing Sheets
Specification includes a Sequence Listing.

(56) References Cited

OTHER PUBLICATIONS

Kim, Y, et al., "Suppression of ß-N-acetylglucosaminidase in the N-glycosylation pathway for complex glycoprotein formation in Drosophila S2 cells," Glycobiology, 2009, vol. 19(3), pp. 301-308.
Léonard, R., et al., "The *Drosophila* fused lobes Gene Encodes an N-Acetylglucosaminidase Involved in N-Glycan Processing," *The Journal of Biological Chemistry*, 2006, vol. 281(8), pp. 4867-4875.
Li, N., et al., "Analysis of Receptor Tyrosin Kinase Internalization Using Flow Cytometry," *Methods Mol Biol.*, 2008, vol. 457, pp. 305-317.
Mabashi-Asazuma, H., et al., "A novel baculovirus vector for the production of nonfucosylated recombinant glycoproteins in insect cells," *Glycobiology*, 2014, vol. 24(3), pp. 325-340.
Mabashi-Asazuma, H., et al., "Modifying an Insect Cell N-Glycan Processing Pathway Using CRISPR-Cas Technology," *ACS Chem. Biol.*, 2015, vol. 10, pp. 2199-2208.
Natasi, C., et al., "The effect of short-chain fatty acids on human monocyt-derived dendritic cells," *Scientific Reports*, 2015, vol. 5: 16148, pp. 1-10.
Natasi, C., et al., "Butyrate and propionate inhibit antigen-specific CD8* T cell activation by suppression IL-12 production by antigen-presenting cells," *Scientific Reports*, 2017, vol. 7: 14516, pp. 1-10.
Nielsen, M., et al., "Induction of Adhesion-Inhibitory Anatibodies against Placental *Plasmodium falciparum* Parasites by Using Single Domains of VAR2CSA," *Infection and Immunity*, 2009, vol. 77(6), pp. 2482-2487.
Nielsen, M., et al., "Plasmodium falciparum: VAR2CSA expressed during pregnancy-associated malaria is partially resistant to proteolytic cleavage by trypsin," *Experimental Parasitology*, 2007, vol. 117, pp. 1-8.
Nielsen, M., et al., "The Influence of Sub-Unit Composition and Expression System on the Functional Antibody Response in the Development of a VAR2CSA Based Plasmodium falciparum Placental Malaria Vaccine," *PLOS One*, 2015, vol. 10, pp. 1-12.
Palladini, A., et al., "Virus-like particle display of HER2 induces potent anti-cancer responses," *Oncoimmunology*, 2018, vol. 7(3), pp. 1-12.
De Vries, R., et al., "Glycan-Dependent Immunogenicity of Recombinant Soluble Trimeric Hemagglutinin," *Journal of Virology*, 2012, vol. 86(21), pp. 11735-11744.
Rendić, D., et al., "Modulation of Neural Carbohydrate Epitope Expression in *Drosophila melanogaster* Cells," *The Journal of Biological Chemistry*, 2006, vol. 281(6), pp. 3343-3353.
Salanti, A., et al., "Several domains from VAR2CSA can induce *Plasmodium falciparum* adhesion-blocking antibodies," *Malaria Journal*, 2010, vol. 9(11), pp. 1-9.
Shishovs, M., et al., "Struction of AP205 Coat Protein Reveals Circular Permutation in ssRNA Bacteriophages," *J Mol Biol*, 2016, vol. 428, pp. 4267-4279.
Shi, X., et anan, "Protein N-Glycosylation in the Baculorivus-Insect Cell System," *Curr Drug Targets*, 2007, vol. 8(10), pp. 1116-1125.
Toth, A., et al., "A new insect cell glycoengineering approach provides baculovirus- inducible glycogene expression and increases human-type glycosylation efficiency," *J Biotechnol.*, 2014, vol. 0, pp. 19-29.

* cited by examiner

Fig. 2
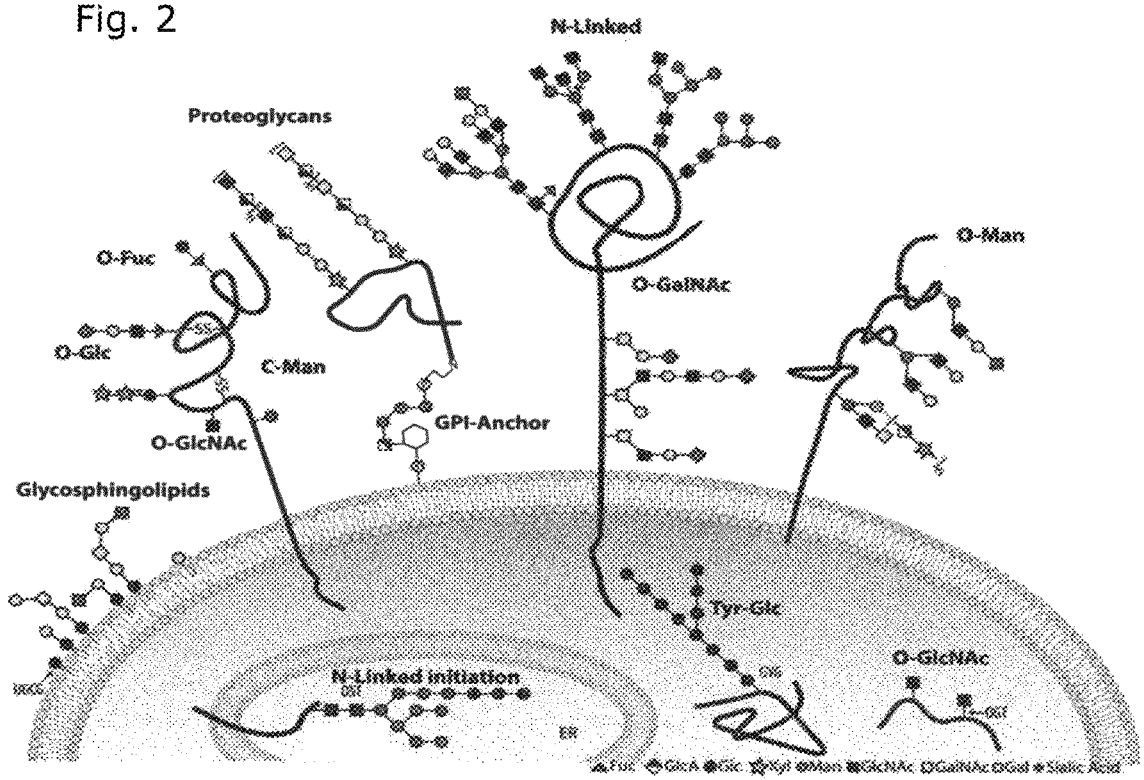
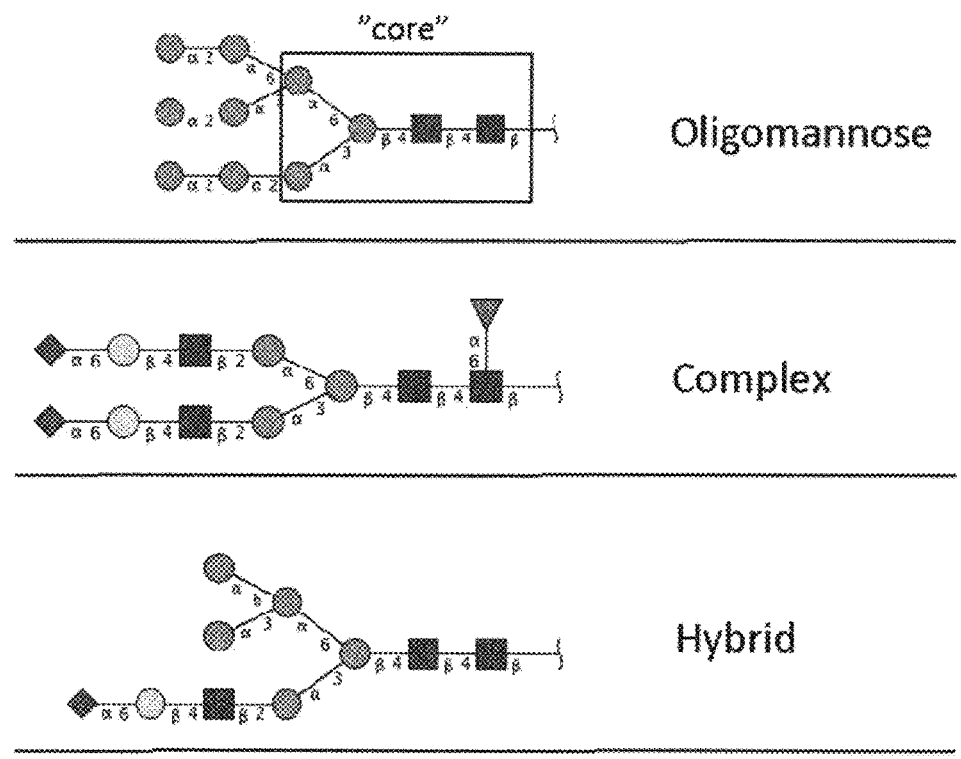
Fig. 3

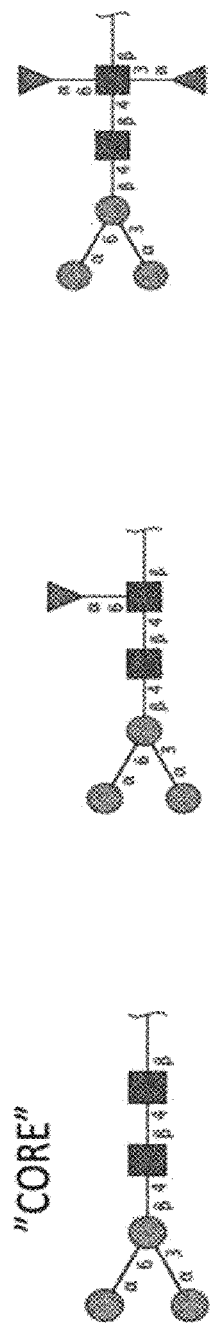
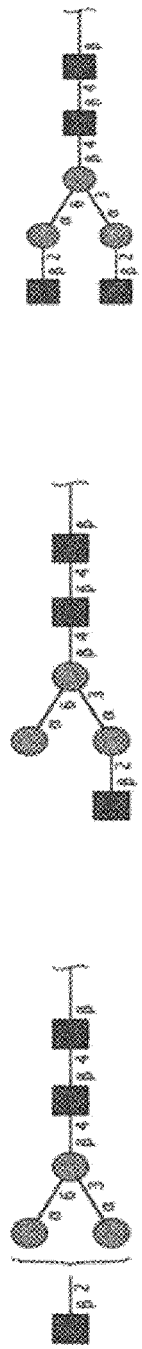
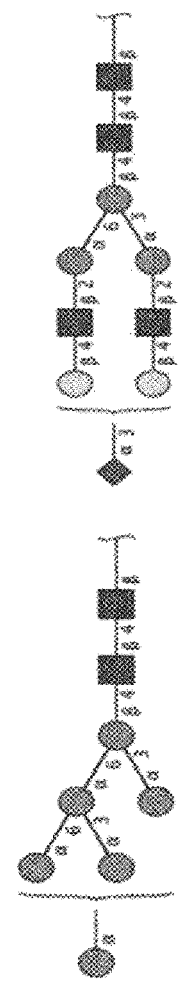
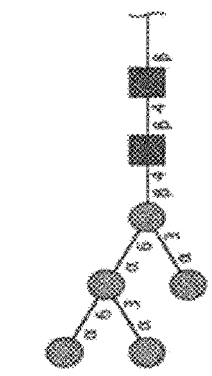
Fig. 4

SEQUENCE LISTING

```
<160> NUMBER OF SEQ ID NOS: 24

<210> SEQ ID NO 1
<211> LENGTH: 24
<212> TYPE: DNA
<213> ORGANISM: Artificial Sequence
<220> FEATURE:
<223> OTHER INFORMATION: Primer sequence

<400> SEQUENCE: 1
ttcgtatcgc cgatcgagtt ggcc                                          24

<210> SEQ ID NO 2
<211> LENGTH: 24
<212> TYPE: DNA
<213> ORGANISM: Artificial Sequence
<220> FEATURE:
<223> OTHER INFORMATION: Primer sequence

<400> SEQUENCE: 2
```

```
aacggccaac tcgatcggcg atac                                          24

<210> SEQ ID NO 3
<211> LENGTH: 24
<212> TYPE: DNA
<213> ORGANISM: Artificial Sequence
<220> FEATURE:
<223> OTHER INFORMATION: Primer sequence

<400> SEQUENCE: 3
ttcgagttaa ttgagactat gcac                                          24

<210> SEQ ID NO 4
<211> LENGTH: 24
<212> TYPE: DNA
<213> ORGANISM: Artificial Sequence
<220> FEATURE:
<223> OTHER INFORMATION: Primer sequence

<400> SEQUENCE: 4
aacgtgcata gtctcaatta actc                                          24

<210> SEQ ID NO 5
<211> LENGTH: 24
<212> TYPE: DNA
<213> ORGANISM: Artificial Sequence
<220> FEATURE:
<223> OTHER INFORMATION: Primer sequence

<400> SEQUENCE: 5
ttcgcaagga acggggctcc gaac                                          24

<210> SEQ ID NO 6
<211> LENGTH: 24
<212> TYPE: DNA
<213> ORGANISM: Artificial Sequence
<220> FEATURE:
<223> OTHER INFORMATION: Primer sequence

<400> SEQUENCE: 6
aacgttcgga gccccgttcc ttgc                                          24

<210> SEQ ID NO 7
<211> LENGTH: 24
<212> TYPE: DNA
<213> ORGANISM: Artificial Sequence
<220> FEATURE:
<223> OTHER INFORMATION: Primer sequence

<400> SEQUENCE: 7
ttcgtgatca ggcgccggac acac                                          24

<210> SEQ ID NO 8
<211> LENGTH: 24
<212> TYPE: DNA
<213> ORGANISM: Artificial Sequence
<220> FEATURE:
<223> OTHER INFORMATION: Primer sequence

<400> SEQUENCE: 8
aacgtgtgtc cggcgcctga tcac                                          24

<210> SEQ ID NO 9
<211> LENGTH: 24
<212> TYPE: DNA
<213> ORGANISM: Artificial Sequence
```

```
<220> FEATURE:
<223> OTHER INFORMATION: Primer sequence

<400> SEQUENCE: 9
ttcgcgctct ggcggatcag ccgc                                  24

<210> SEQ ID NO 10
<211> LENGTH: 24
<212> TYPE: DNA
<213> ORGANISM: Artificial Sequence
<220> FEATURE:
<223> OTHER INFORMATION: Primer sequence

<400> SEQUENCE: 10
aacgcggctg atccgccaga gcgc                                  24

<210> SEQ ID NO 11
<211> LENGTH: 24
<212> TYPE: DNA
<213> ORGANISM: Artificial Sequence
<220> FEATURE:
<223> OTHER INFORMATION: Primer sequence

<400> SEQUENCE: 11
ttcgaatatc gcgagggtcg cgat                                  24

<210> SEQ ID NO 12
<211> LENGTH: 24
<212> TYPE: DNA
<213> ORGANISM: Artificial Sequence
<220> FEATURE:
<223> OTHER INFORMATION: Primer sequence

<400> SEQUENCE: 12
aacatcgcga ccctcgcgat attc                                  24

<210> SEQ ID NO 13
<211> LENGTH: 24
<212> TYPE: DNA
<213> ORGANISM: Artificial Sequence
<220> FEATURE:
<223> OTHER INFORMATION: Primer sequence

<400> SEQUENCE: 13
gcaaggaacg gggctccgaa cgtt                                  24

<210> SEQ ID NO 14
<211> LENGTH: 22
<212> TYPE: DNA
<213> ORGANISM: Artificial Sequence
<220> FEATURE:
<223> OTHER INFORMATION: Primer sequence

<400> SEQUENCE: 14
caacgtttgg agcaaaagat tc                                    22

<210> SEQ ID NO 15
<211> LENGTH: 23
<212> TYPE: DNA
<213> ORGANISM: Artificial Sequence
<220> FEATURE:
<223> OTHER INFORMATION: Primer sequence

<400> SEQUENCE: 15
aaccacctac ctctttgacc ttc                                   23
```

<210> SEQ ID NO 16
<211> LENGTH: 19
<212> TYPE: PRT
<213> ORGANISM: Artificial Sequence
<220> FEATURE:
<223> OTHER INFORMATION: Synthetic peptide

<400> SEQUENCE: 16

Met Lys Leu Cys Ile Leu Leu Ala Val Val Ala Phe Val Gly Leu Ser
1               5                   10                  15

Leu Gly Gly

<210> SEQ ID NO 17
<211> LENGTH: 14
<212> TYPE: PRT
<213> ORGANISM: Artificial Sequence
<220> FEATURE:
<223> OTHER INFORMATION: Synthetic peptide

<400> SEQUENCE: 17

Gly Lys Pro Ile Pro Asn Pro Leu Leu Gly Leu Asp Ser Thr
1               5                   10

<210> SEQ ID NO 18
<211> LENGTH: 13
<212> TYPE: PRT
<213> ORGANISM: Artificial Sequence
<220> FEATURE:
<223> OTHER INFORMATION: Synthetic peptide

<400> SEQUENCE: 18

Ala His Ile Val Met Val Asp Ala Tyr Lys Pro Thr Lys
1               5                   10

<210> SEQ ID NO 19
<211> LENGTH: 114
<212> TYPE: PRT
<213> ORGANISM: Artificial Sequence
<220> FEATURE:
<223> OTHER INFORMATION: Synthetic peptide

<400> SEQUENCE: 19

Met Val Asp Thr Leu Ser Gly Leu Ser Ser Glu Gln Gly Gln Ser Gly
1               5                   10                  15

Asp Met Thr Ile Glu Glu Asp Ser Ala Thr His Ile Lys Phe Ser Lys
                20                  25                  30

Arg Asp Glu Asp Gly Lys Glu Leu Ala Gly Ala Thr Met Glu Leu Arg
            35                  40                  45

Asp Ser Ser Gly Lys Thr Ile Ser Thr Trp Ile Ser Asp Gly Gln Val
        50                  55                  60

Lys Asp Phe Tyr Leu Tyr Pro Gly Lys Tyr Thr Phe Val Glu Thr Ala
65                  70                  75                  80

Ala Pro Asp Gly Tyr Glu Val Ala Thr Ala Ile Thr Phe Thr Val Asn
                85                  90                  95

Glu Gln Gly Gln Val Thr Val Asn Gly Lys Ala Thr Lys Gly Asp Ala
            100                 105                 110

His Ile

<210> SEQ ID NO 20
<211> LENGTH: 11
<212> TYPE: PRT
<213> ORGANISM: Artificial Sequence

```
<220> FEATURE:
<223> OTHER INFORMATION: Synthetic peptide

<400> SEQUENCE: 20

Gly Ser Gly Thr Ala Gly Gly Ser Gly Ser
1               5                   10

<210> SEQ ID NO 21
<211> LENGTH: 11
<212> TYPE: PRT
<213> ORGANISM: Artificial Sequence
<220> FEATURE:
<223> OTHER INFORMATION: Synthetic peptide

<400> SEQUENCE: 21

Gly Thr Ala Ser Gly Gly Ser Gly Gly Ser Gly
1               5                   10

<210> SEQ ID NO 22
<211> LENGTH: 18
<212> TYPE: PRT
<213> ORGANISM: Artificial Sequence
<220> FEATURE:
<223> OTHER INFORMATION: Synthetic peptide

<400> SEQUENCE: 22

Met Lys Leu Cys Ile Leu Leu Ala Val Val Ala Phe Val Gly Leu Ser
1               5                   10                  15

Leu Gly

<210> SEQ ID NO 23
<211> LENGTH: 29
<212> TYPE: PRT
<213> ORGANISM: Artificial Sequence
<220> FEATURE:
<223> OTHER INFORMATION: Synthetic peptide

<400> SEQUENCE: 23

Trp Ser His Pro Gln Phe Glu Lys Gly Gly Gly Ser Gly Gly Gly Ser
1               5                   10                  15

Gly Gly Ser Ser Ala Trp Ser His Pro Gln Phe Glu Lys
            20                  25

<210> SEQ ID NO 24
<211> LENGTH: 4
<212> TYPE: PRT
<213> ORGANISM: Artificial Sequence
<220> FEATURE:
<223> OTHER INFORMATION: Synthetic peptide

<400> SEQUENCE: 24

Glu Pro Glu Ala
1
```

GLYCO-ENGINEERED IMMUNIZATION ANTIGENS

CROSS-REFERENCE TO RELATED APPLICATIONS

This application is a national stage filing under 35 U.S.C. 371 of PCT/EP2020/050591 filed Jan. 10, 2020, which was published by the International Bureau in English on Jul. 16, 2020, and which claims priority from European Application No 19151218.5, filed Jan. 10, 2019, each of which is hereby incorporated in its entirety by reference in this application.

REFERENCE TO SEQUENCE LISTING SUBMITTED ELECTRONICALLY

The official copy of the sequence listing is submitted electronically via EFS-Web as an ASCII formatted sequence listing with a file named I88449_0064_4_Seq_List.txt, created on Jul. 12, 2021, and having a size of 6,073 bytes, which is identical to the sequence listing submitted for International Application No. PCT/EP2020/050591 on Jan. 10, 2020. The sequence listing contained in this ASCII formatted document is part of the specification and is herein incorporated by reference in its entirety.

FIELD OF THE INVENTION

The present invention relates to the field of active immunization. In particular, the present invention provides immunization antigens that have been glyco-engineered to include non-native glycosylation patterns with a view to enhance their properties as antigens for use in such areas as vaccination and antibody production. The invention also pertains to means and methods for producing the glyco-modified antigens as well of methods and uses of the glyco-modified antigens.

BACKGROUND OF THE INVENTION

Protein therapeutics such as monoclonal antibodies (mAbs), peptides and recombinant proteins, represent a large group of developing products in the biopharmaceutical industry. The majority of biological FDA-approved products are recombinant glycoproteins, which are used in treatment against a range of diseases, such as metabolic disorders, autoimmune diseases, and cancer. These products are produced in a wide variety of platforms, such as mammalian expression systems, including CHO and human cell lines, and non-mammalian expression systems, such as bacterial, yeast, plant and insect.

The most appropriate expression system for a specific therapeutic protein depends on the particular protein to be expressed and the intended usage. In the past, proteins with therapeutic capabilities were derived directly from the source, for example humans or pigs. Examples hereof are insulin, which was derived from pancreatic tissue and albumin derived from blood plasma. However, assuring reproducibility, purity, and safety was difficult with the emergence of genetic engineering technology this led to the development of recombinant expression systems for protein production.

Different expression systems have different advantages, but certain therapeutics have glycosylation requirements that currently mean that primarily CHO and other mammalian systems can be used for their production. Other expression systems have advantages like speed and ability to produce difficult proteins.

Glycosylation is generally important to consider when producing vaccine antigens. Especially N-linked glycans are important, as they influence glycoprotein half-life, dictate migration, ensure protein stability, and mediate cell signalling.

The most common expression systems and their glycosylation characteristics are described in the following.

Bacteria as an Expression System

In 1982 the first recombinant biopharmaceutical was approved. This was insulin (by Eli Lilly & Co.'s Humulin®) and it was produced in *Escherichia coli*. *E. coli* has since been used to produce commercially approved non-glycosylated therapeutic proteins, such as cytokines, and monoclonal antibodies and enzymes. Bacteria generally do not glycosylate proteins, as they lack glycosylation machinery. Due to the inability to add N-glycans to proteins, bacteria have a limitation in production compared with more complex hosts for proteins that require post-translational modifications (PTMs). However, the bacterium *Campylobacter jejuni* has exhibited a glycosylation machinery, which has successfully been transferred to *E. coli*. Although this is highly relevant for recombinant protein production, additional optimizations to establish a cost-effective process are still needed.

Yeast as an Expression System

Yeast-based systems have been extensively used for recombinant protein expression. Yeast and filamentous fungi offer numerous advantages as recombinant protein expression systems when compared with mammalian cell culture, including high recombinant protein titers, short fermentation times, and the ability to grow in chemically defined media. *Saccharomyces cerevisiae* is the expression system for approximately 20% of all biopharmaceuticals, including insulin, hepatitis vaccines, and human serum albumin. Yeasts can be grown in industrial scale and they represent very robust expression, capable of folding proteins and secreting these into the medium. Furthermore, they also present well characterized N-glycosylation, which is often hyper-mannosylation. To produce better drugs many efforts have been made to humanize the N-glycosylation in yeasts, and in 2006 Hamilton et al managed to construct a *Pichia pastoris* cell line that adds 90.5% of double-sialylated N-glycan structures on purified erythropoietin (EPO).

Plant Cells as an Expression System

Plant cells can be cultured in basal culture medium and are easily scaled up. Plant cells do not contain endotoxins like *E. coli* and they do not represent the same disadvantages as recombinant protein production in whole plants. Plant cells show greater similarity to human N-glycans than yeast does. However, plant cells are also known to express α1,3-fucose and β1,2-xylose, which both are considered immunogenic to the human immune system. In 2012 the first plant-based therapeutic was approved by the FDA. Elelyso (ProTalix BioTherapeutics), which is made in carrot cells and carry α1,3-fucose and β1,2-xylose, is intended for patients suffering from the lysosomal storage disease known as Gaucher disease. These individuals lack the enzyme glucocerebrosidase and previous treatment for this condition has been through administration of recombinant glucocerebrosidase produced from mammalian cells. As this production in mammalian cells is relatively expensive, efforts were put into producing glucocerebrosidase in a cheaper system. Remarkably, the plant-produced glucocerebrosidase does not seem to cause adverse immune reactions in humans.

Mammalian Cells as an Expression System

More than 50% of therapeutic proteins available on the market are produced using mammalian cells. Generally, mammalian expression systems are preferred for manufacture of biopharmaceuticals that are large and complex proteins and which require post translational modifications (PTMs, most notably glycosylation) as these usually are relatively similar to proteins produced in humans. Moreover, in the case of mammalian cell lines, and animal cell lines in general, most proteins can be secreted directly into the growth medium, which is advantageous compared with bacteria/prokaryotes, where cell lysis is needed to extract protein and potential subsequent refolding of the protein. The most common mammalian (non-human) cell lines used for therapeutic protein production include murine myeloma cells (NS0 and Sp2/0), Chinese hamster ovary (CHO) cells, and baby hamster kidney (BHK21) cells. However, these non-human mammalian cell lines also have disadvantages. They produce glycosylation that is not expressed in humans, more specifically galactose-$\alpha$1,3-galactose ($\alpha$-gal) and N-glycolylneuraminic acid (Neu5Gc). Antibodies against both of these N-glycans are found in human circulation, therefore therapeutic drugs are screened during cell line development and production for an acceptable glycan profile. Glycan profiles are considered a critical quality parameter for therapeutic proteins.

Insect Cells as an Expression System

Insect cells are easily cultured and can secrete correctly folded and posttranslationally modified proteins into the medium. The N-glycans in insect cells are, like plant N-glycans, comparable to human structures, but they are generally simpler. Most proteins produced in insect cell lines carry M3 or F(6)M3 and to some degree also high-mannose structures. The baculovirus expression system (BEVS) is the most common insect expression system and is used for many recombinant expression purposes. This insect cell based expression platform has successfully been used to produce vaccine antigens and virus-like particles. Until now, Cervarix® (GlaxoSmithKline) and FluBlok® (Protein Sciences) have been approved as vaccines by the FDA. Regulatory authorities have also approved Provenge® (Dendreon) which contains an Sf21 cell line produced protein as a component of the autologous prostate-cancer therapy product. The *Spodoptera frugiperda* 9 (Sf9) insect cell line has been glyco-engineered to produce more complex N-glycosylation. There are, however, still relatively high levels of F(6)M3 left as well as intermediate glycan structures.

Some insect cells, such as the *Trichoplusia ni* derived High Five™ and Tni PRO™ cells, glycosylate in a similar M3 structure as Sf9 and *Drosophila* Schneider 2 (S2) cells, but with an immunogenic $\alpha$1,3-linked fucose rather than a $\alpha$1,6-linked as the Sf9 and S2 cells. Efforts have been made to remove fucosylation on proteins expressed in Sf9, High Five™ and Tni PRO™. The approach was not to directly target the genes responsible for the attachment of core $\alpha$1,3- and $\alpha$1,6-fucose, fut11/12 and FucT6 respectively, but instead targeting both $\alpha$1,3- and $\alpha$1,6-linked fucose at the same time by inserting a gene for an enzyme that consumes the immediate precursor to GDP-L-fucose to produce GDP-D-rhamnose, which would remove any substrate for fucose addition. This was successful, however, Mabashi-Asazuma et al. (2014), Glycobiology 24: 325-340, saw issues with long-term stability of the cell lines.

The S2 insect cell line was originally established in 1971 by Imogene Schneider. Since then around 100 *Drosophila* cell lines have been obtained out of which 12 are easily cultivated. However, the primary cell lines being used for recombinant protein production are two of the original Schneider cell lines: Schneider's 2 (S2) and 3 (S3). Both S2 and S3 can be genetically modified to express recombinant proteins independent of viral infection, unlike BEVS. However, only S2 cells have been used to produce vaccine antigens for clinical trials. Stably transfected S2 cells can grow at high cell densities (up to $50 \times 10^6$ cells/mL) in suspension and S2 based production processes are scalable. It is well established that S2 cell recombinant proteins carry pauci-mannosidic glycans and often also attach core $\alpha$1,6-fucose. In addition, the present inventors have also detected small amounts of high-mannose structures and A1.

The two most prevalent N-linked glycan structures found on protein secreted from S2 and Sf9 cells are M3 and F(6)M3. In the High Five™ cell line further two structures are also found, the immunogenic F(3)M3 and F(3)F(6)M3.

To summarize, the different expression systems discussed above can be summarized as follows:

| | Expression System | | | | |
|---|---|---|---|---|---|
| Desired characteristics | Bacteria | Yeast | Plant cell culture | Insect cell culture | Mammalian cell culture |
| Cell growth | Rapid | Rapid | Slow | Slow | Slow |
| Complexity of growth medium | Minimum | Minimum | Complex | Complex | Complex |
| Cost of growth medium | Low | Low | Low | High | High |
| Expression level | High | Low to high | Low to high | Low to high | Low to moderate |
| Extracellular expression | Secretion to periplasm | Secretion to medium | Secretion to medium | Secretion to medium | Secretion to medium |
| Post tanslational modifications | | | | | |
| Protein folding | Refolding usually required | Re folding may be required | Proper folding | Proper folding | Proper folding |
| N-linked glycosylation | No | Hyper-mannose | Simple, no sialic acid, but xylose and 1,3-fucose | Simple, no sialic acid | Complex |
| O-linked glycosylation | No | Yes | Yes | Yes | Yes |
| Phosphorylation | No | Yes | Yes | Yes | Yes |
| Acetylation | No | Yes | Yes | Yes | Yes |
| Acylation | No | Yes | Yes | Yes | Yes |
| γ-Carboxylation | No | No | No | No | Yes |

Glycosylation and the Immune System

Generally, glycosylation of proteins plays an important role in various parts of vertebrate immune systems:

Antibodies, or immunoglobulins (Ig), are glycoproteins, which are produced by the immune system to target foreign invading pathogens. Igs consist of a variable antigen-binding (Fab) fragment and a constant (Fc) fragment.

Variable Fab regions bind to high diverse molecular structures in proteins, carbohydrate and lipids. Antibodies can exist in a secreted form or as membrane-bound. There are five antibody isotypes. IgA is found in mucosal areas, such as the gut, respiratory tract and urogenital tract, saliva, tears and breast milk. IgD is an antigen receptor on B-cells that have not yet been exposed to antigens. IgE acts as a receptor on the surface of mast cells and basophils and triggers histamine release from these upon cross-binding to antigens; biologically, this action protects against parasitic worms but the reaction is also involved in type I allergy. IgG consists of four different isotypes and is the major antibody involved in immunity against invading pathogens. IgM is expressed on the surface of B cells as a monomer, but also in a secreted form as a di- or pentamer, which eliminates pathogens in the early stages of the B-cell mediated humoral response before sufficient levels of IgG are reached. Core fucose on the glycan structure limits the IgG binding to the IgG Fc receptor, which results in decreased antibody-dependent cell-mediated cytotoxicity.

Antibodies are produced by the adaptive immune system, more specifically by B cells. B cells mature in the bone marrow and on release, each expresses a unique antigen-binding receptor on its membrane. When a naïve B-cell first encounters the antigen that matches its membrane-bound antibody, the binding of the antigen to the antibody (in a process the normally requires concurrent stimulation from T helper lymphocytes that recognize processed antigen presented by the B-cell on its surface) causes the B-cell to divide rapidly into memory B-cells and effector B-cells. The memory B-cells have longer life span than their parent B-cell, and they continue to express membrane-bound antibody similar to their parent B-cell. Effector cells produce the antibody in a secreted form. Effector cells only survive for a few days; however, they secrete considerable amounts of antibodies. Secreted antibodies are the major effector of humoral immunity. Some antibodies play their role simply through the binding to the target epitopes to block or induce signal transduction, whereas other antibodies bind the antigen and then recruit circulating lymphoid and myeloid cells to kill the invading pathogen by antibody-mediated effector functions (i.e., complement-dependent cytotoxicity, antibody-dependent cell-mediated cytotoxicity, and antibody-dependent cellular phagocytosis).

Dendritic cells (DCs) are a primary link between the innate and the adaptive immune system in mammals. Their primary function is to present digested antigens to T cells. DCs are found in tissues that are in contact with the environment, such as the skin, inner linings of nose, lungs, stomach and intestines. Once a DC is activated, it will migrate to the lymph node and interact with B and T cells. This process shapes the adaptive immune response.

The immature DCs are constantly analyzing their surrounding environment for pathogens via their pattern recognition receptors (PRRs), such as Toll-like receptors (TLRs). These recognize specific repetitive structures found on pathogens. Immature dendritic cells phagocytize pathogens and degrade these into peptides and present them on their cell surface during maturation. The surface presentation is carried out by major histocompatibility complex (MHC) molecules, which present the peptides to T-cells. During maturation, the DCs up-regulate surface receptors, such as CD80, CD86, and CD40 that greatly contribute to T-cell activation. In turn, activated T-cells aid in the full maturation of B-cells and antibody production. DCs carry certain C-type lectin receptors (CLRs) on their surface, which help instruct the DCs as when to induce immune tolerance rather than an immune reaction. Examples of these C-type lectins are the mannose receptor (MR, CD206) and Dendritic Cell-Specific Intercellular adhesion molecule-3-Grabbing Non-integrin (DC-SIGN, CD209). Blood contains monocytes, which can be matured into DCs in vitro.

Innate immune responses are often initiated by macrophage lectins recognizing microbial glycans, which results in phagocytosis. Circulating lectins, such as serum mannose-binding lectin (MBL) and ficolins, bind to pathogen cell surfaces, hereby activating the complement cascade. When immune cells bind to glycans it can also activate intracellular signalling that either triggers or suppresses cellular responses. For example, binding of trehalose dimycolate, a glycolipid found in the cell wall of Mycobacterium tuberculosis by the macrophage C-type lectin Mincle, induces a signalling pathway that causes the macrophage to secrete pro-inflammatory cytokines. However, glycans can also have the opposite effect. For example, the B-lymphocyte carries a lectin called CD22, that when bound to α2,6-linked sialic acis initiates signalling that inhibits activation to prevent self-reactivity. Interestingly, the α2,6-linked sialic acid is also the gateway for the human influenza virus to enter human cells. The lectin of the virus, also called the hemagglutinin, facilitates binding to the host cell membrane and entry inside the cell. This interaction is highly specific. The human influenza virus recognizes α2,6-linked sialic acid and the bird influenza virus recognizes only α2,3-linked sialic acid.

The mannose receptor (MR), or Cluster of Differentiation 206 (CD206) is a C-type lectin, which is found on the surface of macrophages and dendrtic cells. The MR has 8 recognition domains, which recognize terminal mannose, GlcNAc and fucose residues on glycans carried by proteins. MR has higher affinity towards branched mannose structures than linear ones, and preferably pauci-mannose structures. The MR plays a role in antigen uptake and presentation by immature DCs in the adaptive immune system. Upon binding, MR ensures delivery of the bound antigen to the early endosomes, and afterwards to the lysosomes. Here the antigen is degraded and presented on MHC class II molecules, which stimulates and polarizes the adaptive immune response.

Dendritic Cell-Specific Intercellular adhesion molecule-3-Grabbing Non-integrin (DC-SIGN) is, like MR, also a C-type lectin, which is found on the surface of macrophages and dendritic cells. This receptor also recognizes mannose, albeit DC-SIGN has higher specificity towards high-mannose, preferably M9, structures than pauci-mannose structures. DC-SIGN has been shown to bind relatively weak to F(6)M3 and to not bind F(3)M3 at all. DC-SIGN only encompasses one recognition site, however, it forms tetramers with other DC-SIGNs on the DC surface. Once DC-SIGN binds to a glycan or a microorganism it delivers the bound components to late endosomes or lysosomes, where they are destined for degradation. The degraded antigens are presented on MHC class II for T cell presentation. In specific cases it appears that both MR and DC-SIGN deliver antigens to MHC class I molecules.

Mannose Binding Lectin (MBL) is a secreted C-type lectin found in circulation, which recognizes mannose structures. Like the membrane bound MR and DC-SIGN, the recognition is not entirely specific, and MBL binds with higher specificity to high-mannose also recognizes fucose and GlcNAc. MBL encompasses a single receptor, and forms a trimer as a basic unit. When six trimmers aggregate a very strong binding is seen. In contrast to MR and DC-SIGN, MBL is capable of activating the innate immune system. Upon binding to a microorganism or antigen carrying mannose, the MBL activates the complement by the lectin pathway, followed by opsonization and phagocytosis.

To conclude, there is a continued need to provide recombinant proteins having engineered glycosylation designed for particular purposes, in particular when the purpose relates to immunotherapy and vaccination. It is also of value to overcome limitations in the native S2 glycosylation machinery, since this can lead to new and powerful expression systems for industry use, which would enable preparation of new drugs.

OBJECTS OF THE INVENTION

It is an object of embodiments of the invention to provide glyco-engineered antigens for use in immunization technology, including vaccination, which have improved antigenic/immunogenic properties compared to their non-modified counterparts. It is further an object of other embodiments of the invention to provide means and methods for preparation of the glyco-engineered antigens and also to provide methods and uses that employ the glyco-engineered antigens.

SUMMARY OF THE INVENTION

The present inventors have engineered the N-glycosylation pathway in *Drosophila* Schneider 2 (S2) cells to alter glycosylation of recombinant proteins and have investigated whether it was possible to influence the immunological properties of these proteins in vivo.

In an effort to study the effects of glycans on the immune response, the inventors set out to engineer cell lines yielding altered glycosylation and investigate which effects these had in a in vivo mouse model and on immune cells in vitro. The present inventors thus set out to modify the pauci-mannosidic N-linked glycan structure of *Drosophila* Schneider 2 (S2) cells in order to improve the immune response generated by (vaccine) antigens.

The primary model protein for the immunological studies was the VAR2CSA protein. This model protein is particularly interesting, as it is a candidate for a placental malaria vaccine. As a vaccine candidate VAR2CSA would most likely benefit from carrying immunogenic glycans. VAR2CSA recognizes chondroitin sulfate A (CSA) on placental cells. Additionally, this receptor recognizes CSA on most cancer cells. This antigen is especially interesting for studying glycosylation as it functions both as a vaccine antigen, and potentially also as a cancer therapeutic. For the purposes of vaccination, it was of interest to engineer more immunogenic glycan structures.

In a $1^{st}$ aspect the present invention relates to a non-plant polypeptide or protein comprising N-linked glycans that comprise α1,3-linked fucose.

In a $2^{nd}$ aspect, the present invention relates to an immunogenic composition comprising a polypeptide of the first aspect of the invention in admixture with at least one immunological adjuvant and optionally a pharmaceutically acceptable carrier and/or diluent and/or excipient.

In a $3^{rd}$ aspect, the present invention relates to a method for inducing or enhancing a specific immune response in an animal, such as a human being, the method comprising at least one immunization of the animal with an effective amount of the protein or polypeptide of the first aspect of the invention or the composition of the second aspect of the invention.

In a $4^{th}$ aspect, the invention relates to a genetically modified non-plant eukaryotic cell, which comprises at least one heterologous polynucleotide sequence encoding and expressing a heterologous α1,3-fucosyltransferase and/or wherein expression of the α-Man-Ia gene has been reduced or abolished and/or wherein expression of genes encoding enzyme(s) extending glycans beyond Man5 is increased. This aspect also relates to a cell line, such as a clonal cell line, comprising a cell of the $4^{th}$ aspect.

Finally, in a $5^{th}$ aspect, the invention relates to a method for producing an N-glycosylated polypeptide or protein carrying α1,3-fucosyl groups, the method comprising culturing a cell or cell line of the $4^{th}$ aspect of the invention, wherein the cell or cell line expresses a polynucleotide encoding the amino acid sequence of the N-glycosylated polypeptide or protein, and subsequently isolating the N-glycosylated polypeptide or protein from the culture mixture, and optionally subjecting the N-glycosylated polypeptide or protein to further purification.

LEGENDS TO THE FIGURE

FIG. 1: Glycans discussed in the present application.

Dark square: N-aetylglucosamine (GlcNAc), dark circle: glucose, light grey circle: mannose, triangle: fucose, light grey circle: galactose, diamond: sialic acid.

FIG. 2: Schematic presentation of different glycosylation patterns in mammalian cells.

FIG. 3: The three categories of N-Glycans, oligomannose, complex and hybrid.

Dark square: N-aetylglucosamine (GlcNAc), light grey circle: mannose, triangle: fucose, light grey circle: galactose, diamond: sialic acid.

FIG. 4: Examples of structures and their nomenclature of N-linked glycans.

Dark square: N-acetylglucosamine (GlcNAc), light grey circle: mannose, triangle: fucose, light grey circle: galactose, diamond: sialic acid.

Figure 5:
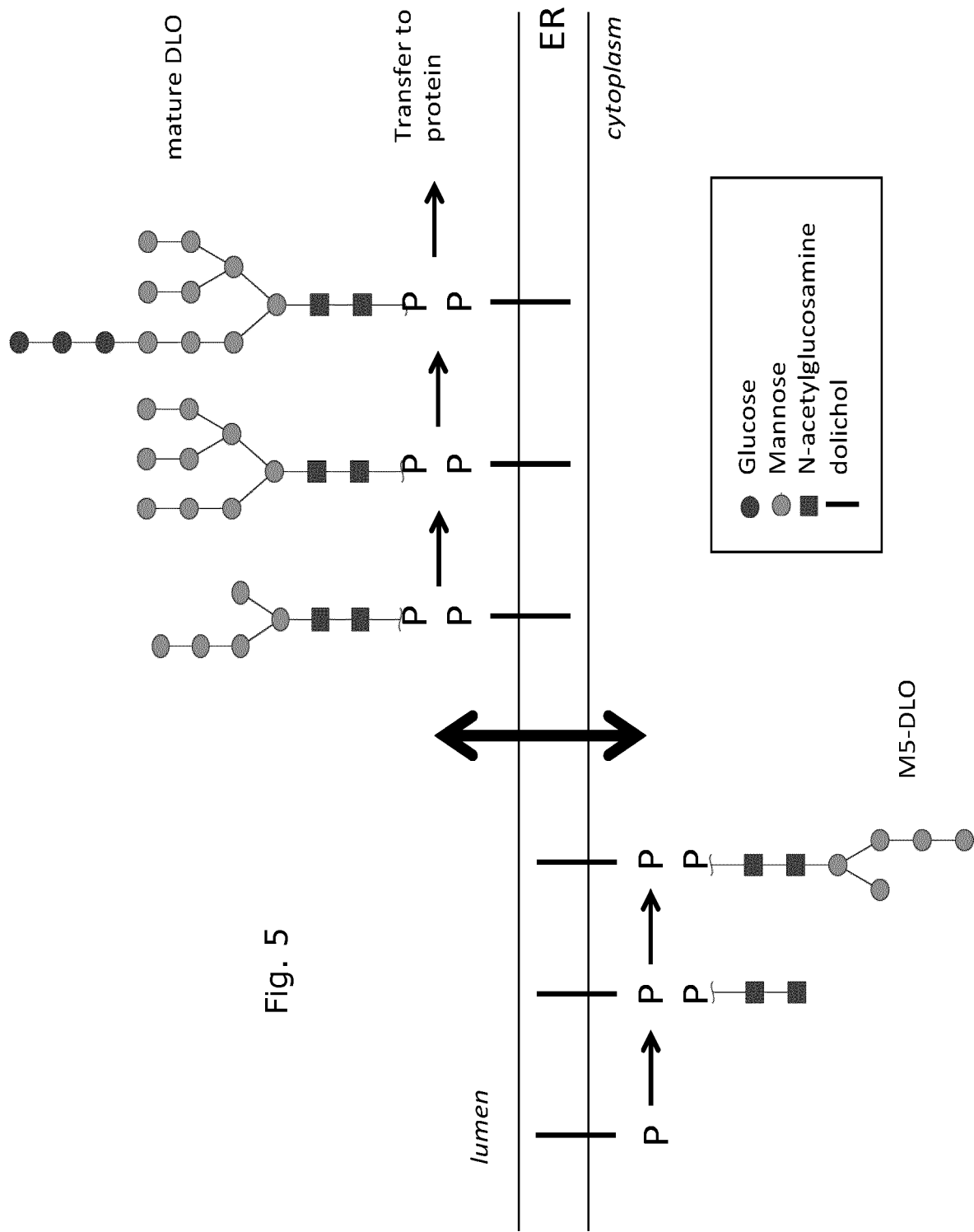

FIG. 5: Schematic representation of the synthesis of dolichol-P-P-GlcNAc2Man9Glc3 (mature DLO).

Figure 6:
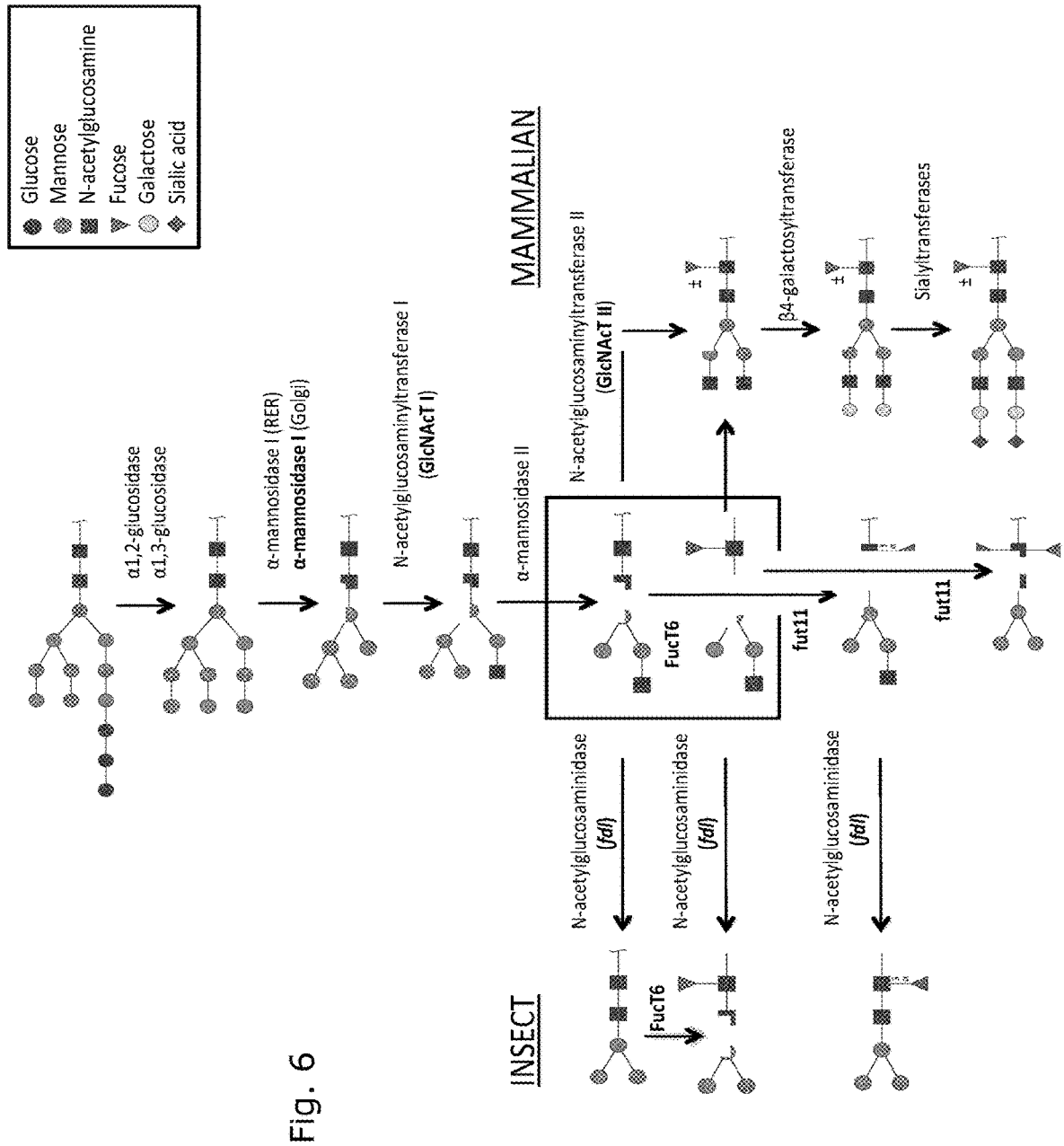

FIG. 6: Figure of M9Glc3 degradation pathway and differentiation of insect vs. mammalian glycan shaping pathway.

FucT6 (α1,6-fucosylatransferase), fut11 (α1,3-fucosylatransferase), and the other genes presented in bold are modified in the present disclosure.

Figure 7:
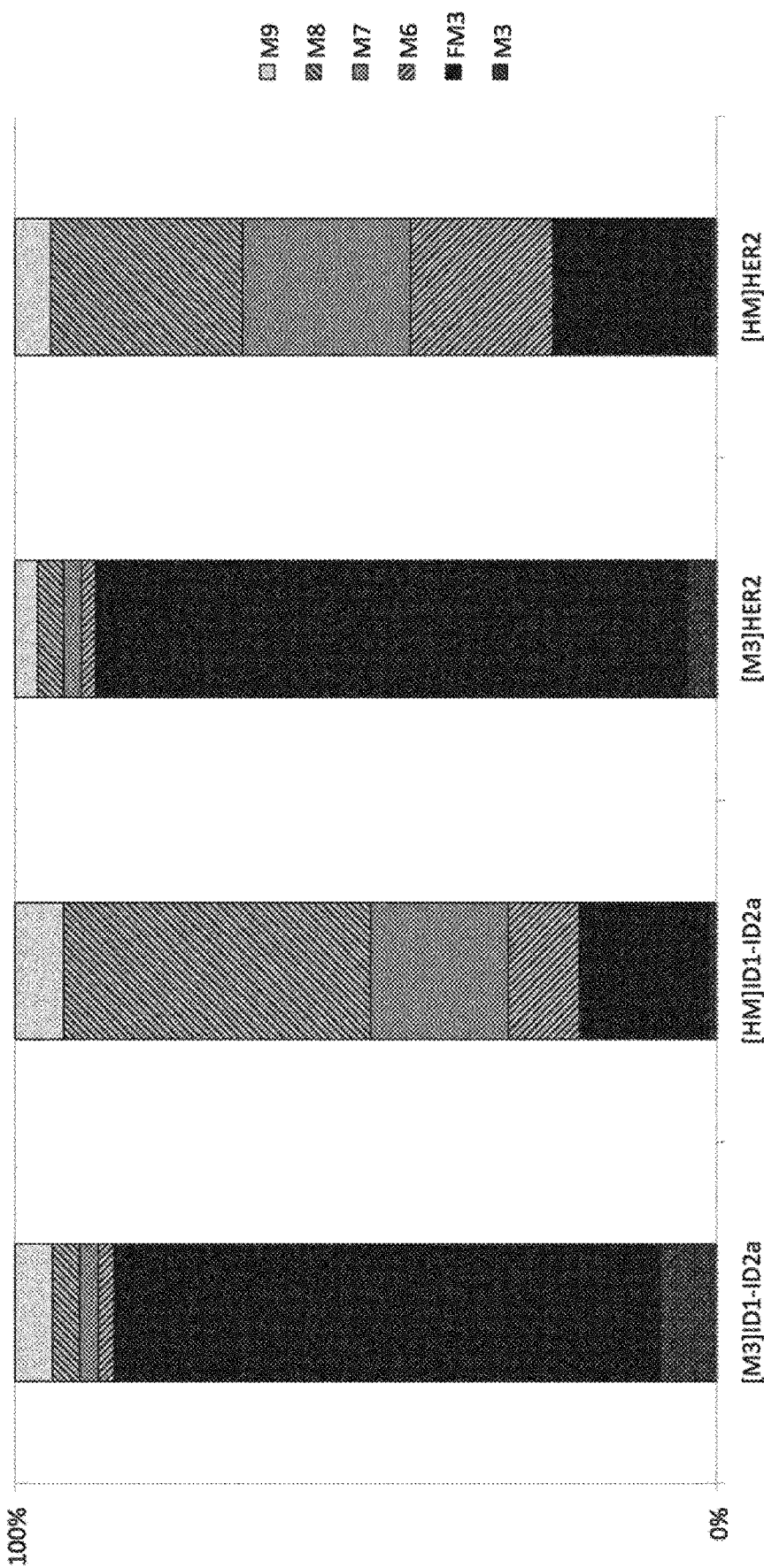

FIG. 7: Bar graph presentation of glycan composition of protein constructs from Example 2.

A recombinant ID1-ID2a construct with added V5-tag, HIS-tag, and SpyTag (the latter for coupling to VLPs) and a recombinant HER2-SpyC were expressed in S2-WT cells ([M3]ID1-ID2a and [M3]HER2) and the same constructs were expressed in S2-Δα-Man-Ia ([HM]ID1-ID2a and [HM]HER2). Glycans present in less than 7% of the total glycan pool (such as M4, FA1, and M5) were excluded from this bar-graph presentation.

Figure 8:
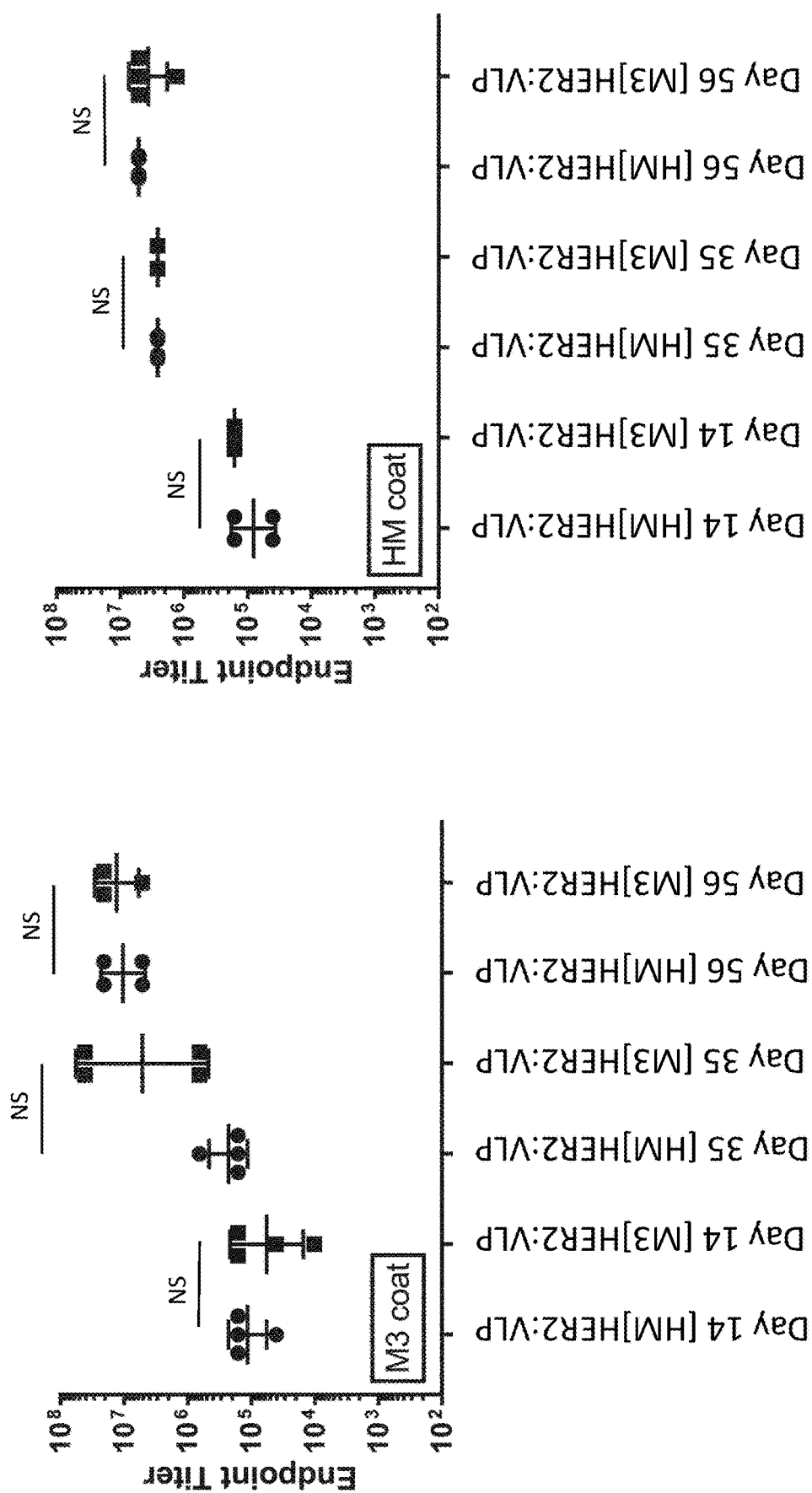

FIG. 8: HER2 glycan dependent induction of antibodies against HER2.

Female BALB/c mice from 6-8 weeks of age (4 per group) were immunized three times intramuscularly with 5 µg purified [HM]HER2 or [M3]HER2 coupled to VLPs and formulated with AddaVax. Blood samples were taken 14 days post immunization at Days 14, 35 and 56. The horizontal line represents the geometric mean per group. The statistical analysis was performed by a non-parametric, two-tailed, Mann-Whitney Rank Sum Test, with statistical significance being defined at threshold P<0.05, with cut-off calculated by (mean[PBS])+(3*standard deviation[PBS]). Differences between groups were NS=not significant.

Figure 9:
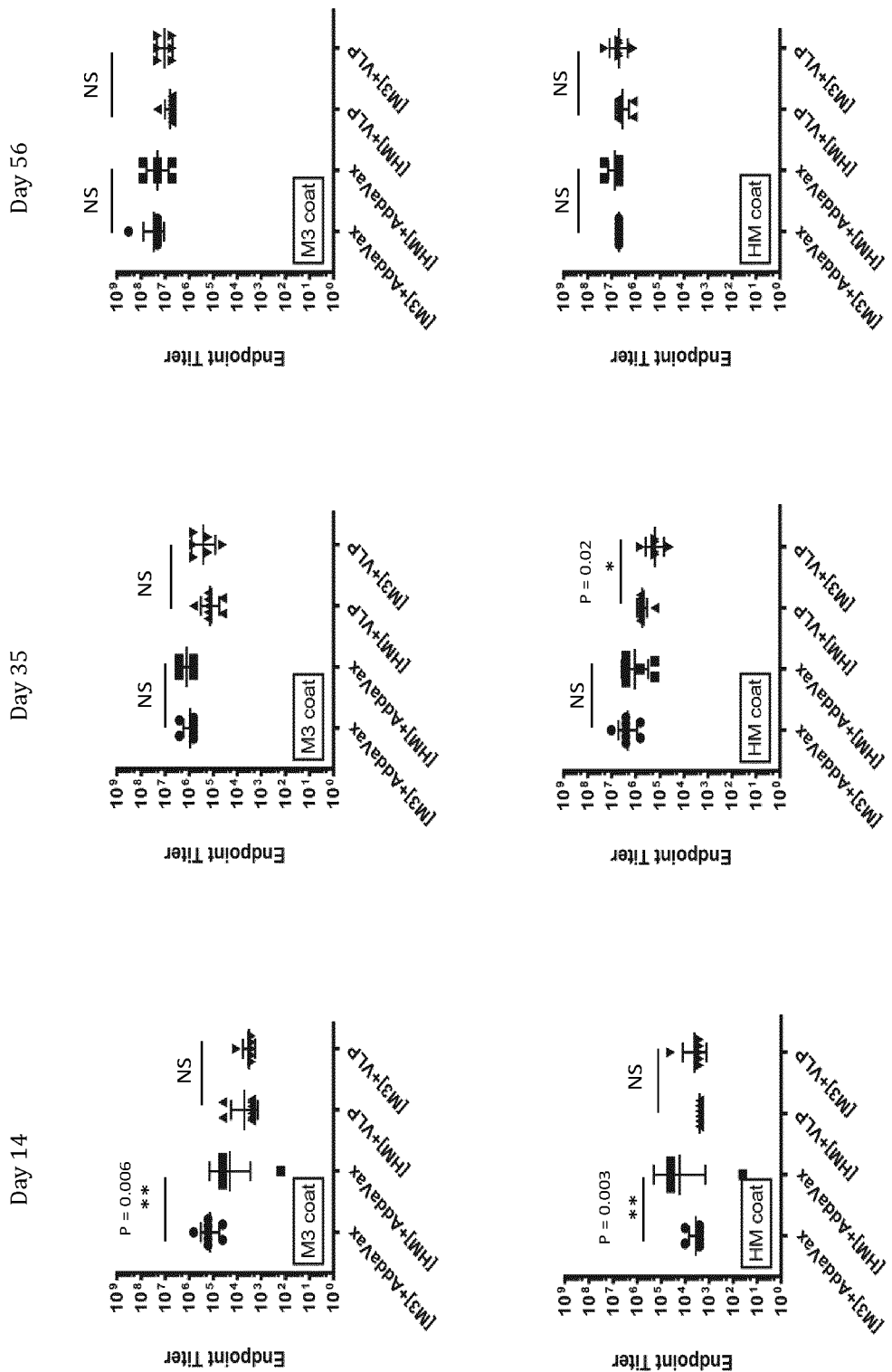

FIG. 9: ID1-ID2a glycan dependent induction of antibodies against ID1-ID2a.

Female BALB/c mice were immunized in groups of 8 with ID1-ID2a with either primarily M3 glycosylation of primarily high-mannose (HM) glycosylation, formulated with two different adjuvants: AddaVax or coupled to a VLP. Total IgG serum titers were measured by ELISA on serum samples taken on day 14, 35, and 56, and plates were coated with either M3 ID1-ID2a (upper row) or HM ID1-ID2a (lower row). The horizontal line represents the geometric mean per group. The statistical analysis was performed by a non-parametric two-tailed, Mann-Whitney Rank Sum Test with statistical significance being defined at threshold P<0.05, with cut-off calculated by Geometric mean of PBS sample+3* Standard deviation of PBS samples. Significant difference between groups are *, P<0.05; **, P<0.01; NS, not significant.

Figure 10:
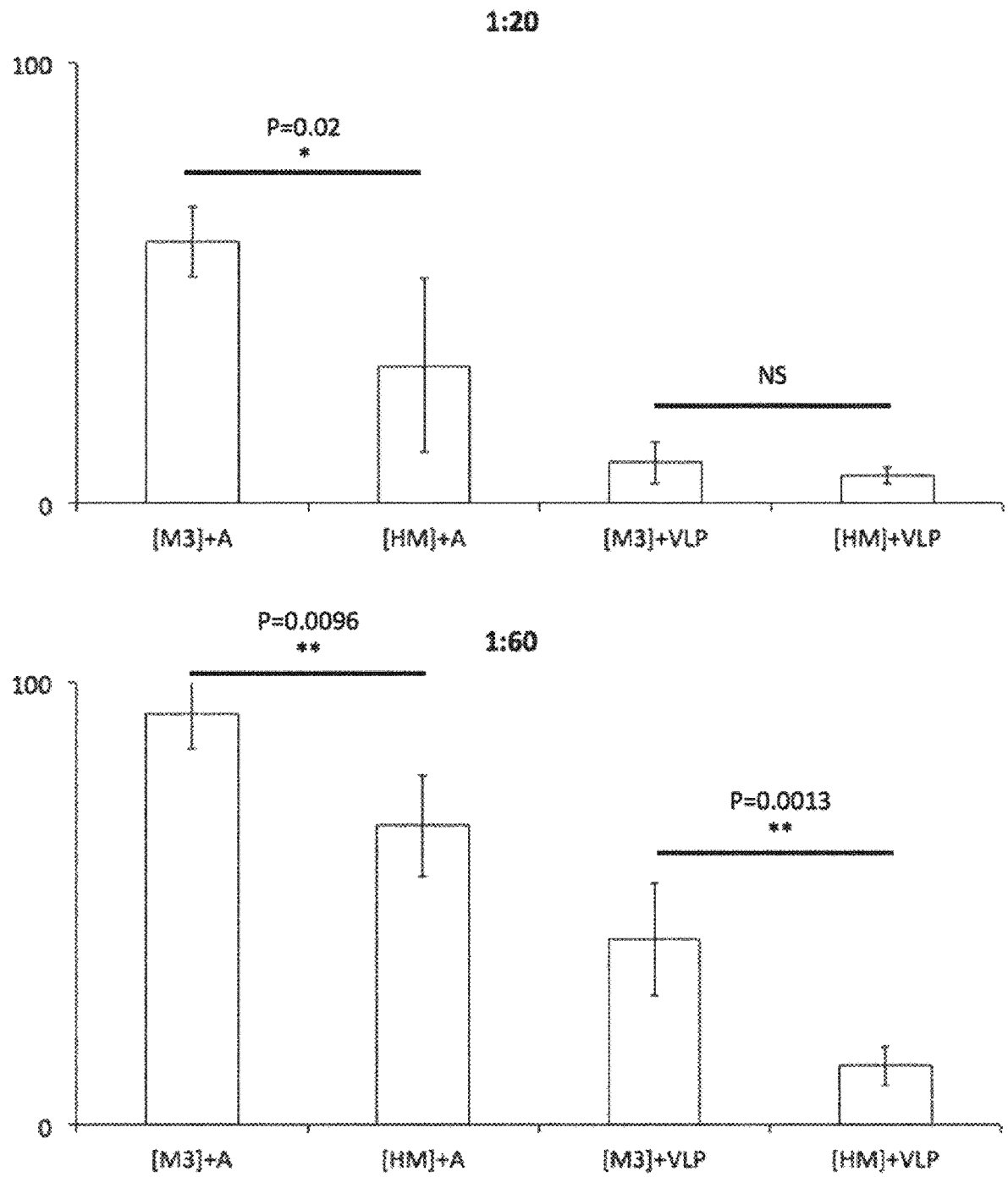

FIG. 10: Antibody abilities to prevent binding of IE to CSA.

Upper graph is 1:20 dilution and lower graph is 1:60 dilution of serum. Error bars are standard deviations of triplicate reactions. The assay was performed once. The Y-axis represents binding % of IE binding to CSA. The statistical significance was determined by paired Student's t-test (normal distribution deemed valid by Q-Q plot) with significance being *, p<0.05; **p<0.01, NS=Not Significant.

Figure 11:
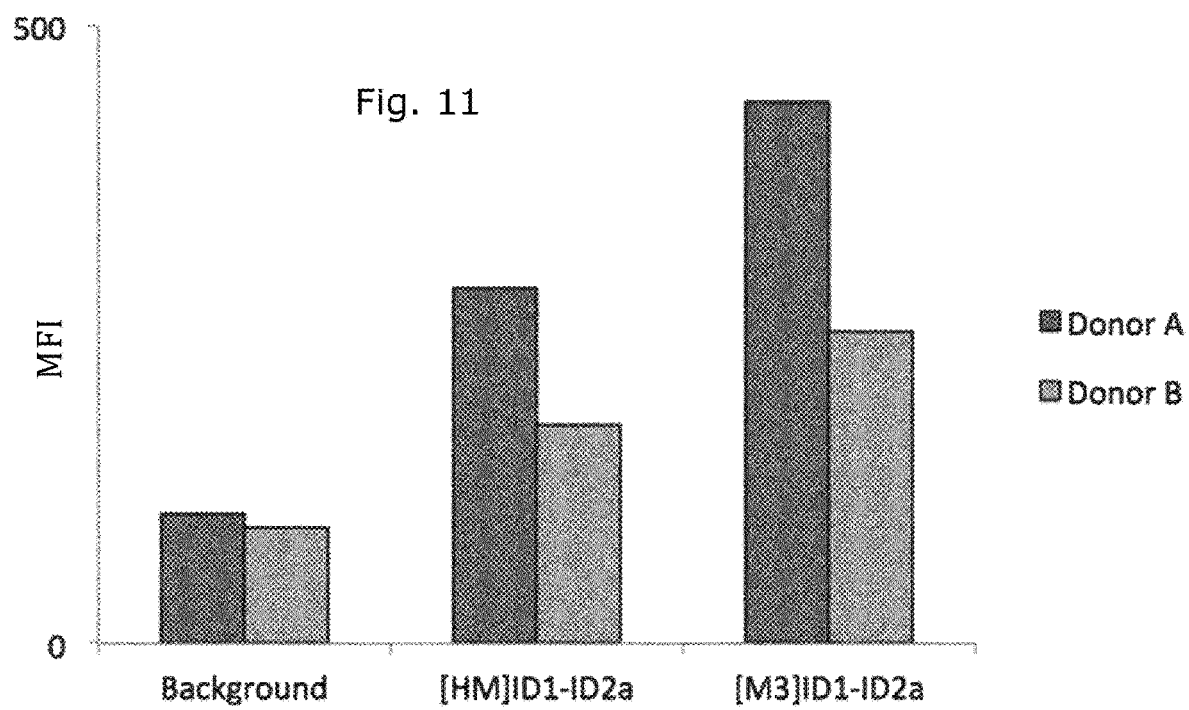

FIG. 11. Graph showing mean fluorescence intensities (MFI, y-axis) measured by flow cytometry on pulsed DCs from two donors with FITC-labeled [M3]ID1-ID2a and [HM]ID1-ID2a (not coupled to VLPs) for 2 minutes.

Figure 12:
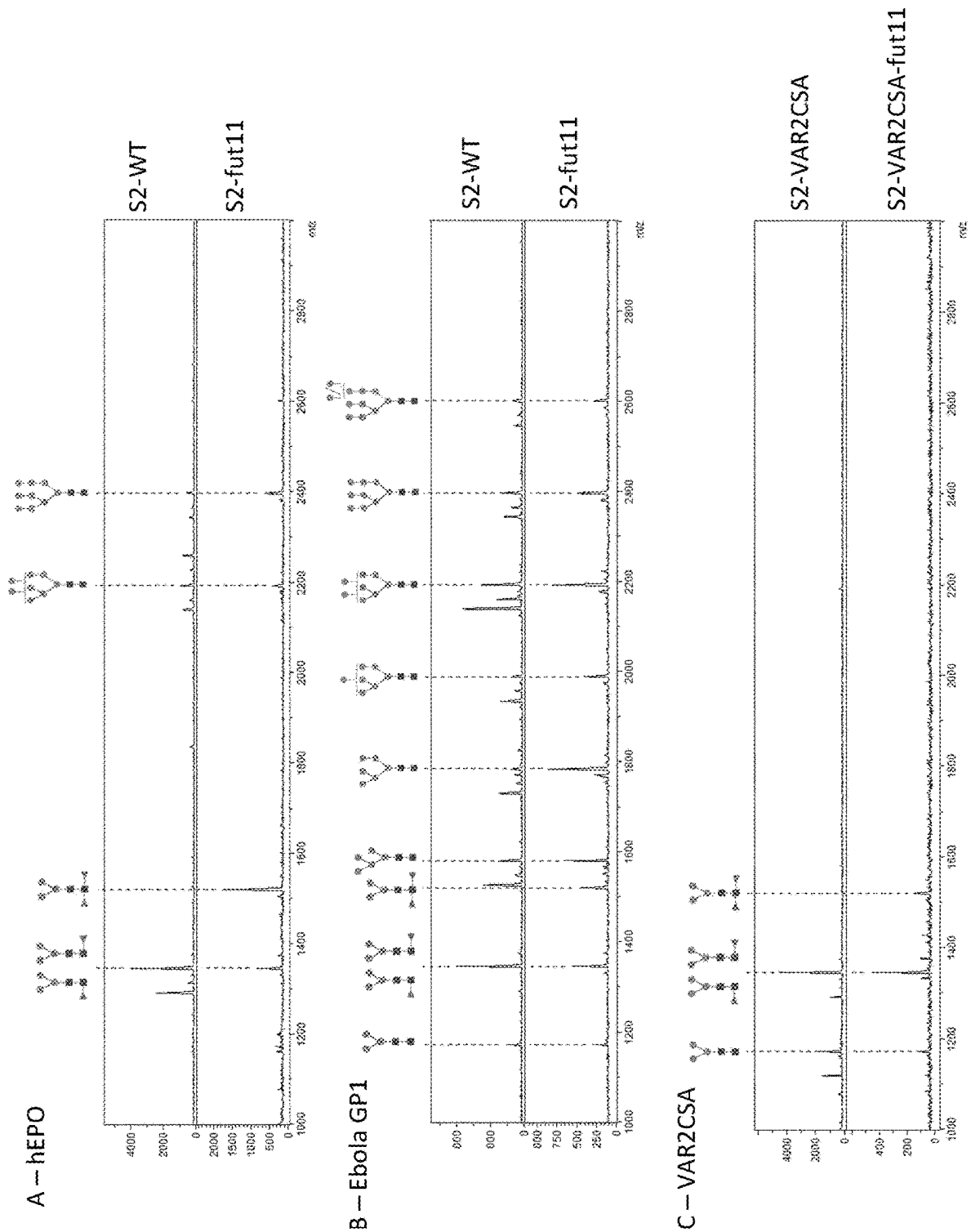

FIG. 12. Mass spectrometry of N-glycosylated proteins.

hEPO and Ebola GP1 were expressed in S2-WT cells and in S2-fut11; VAR2CSA was expressed in S2-VAR2CSA and S2-VAR2CSA-fut11. Purified protein from all six cell lines was analyzed by MALDI-TOF. A: hEPO, B: Ebola GP1, C: VAR2CSA.

Figure 13:
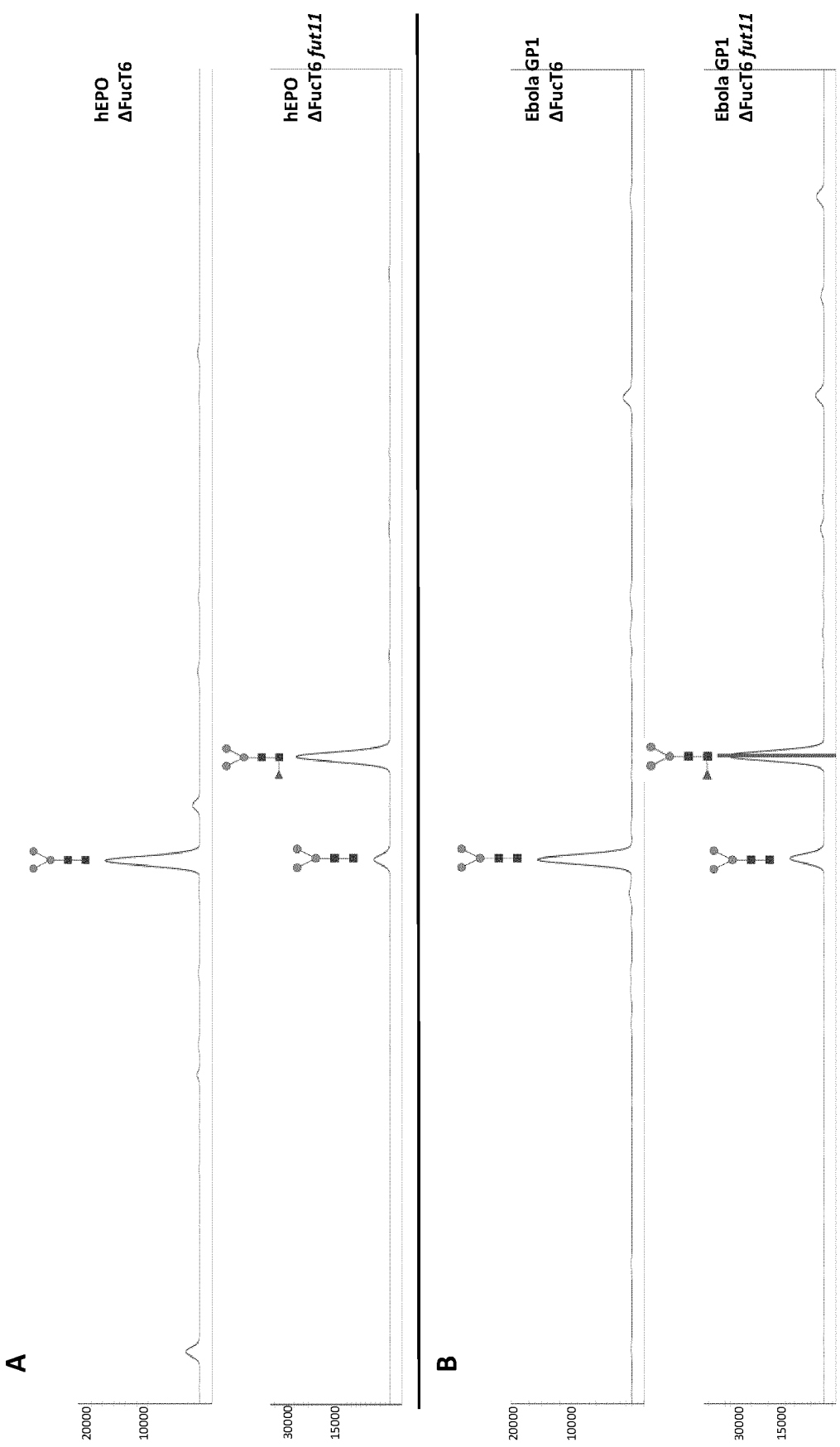

FIG. 13. Capillary electrophoresis of N-glycosylated proteins produced in ΔfucT6 and ΔfucT6-fut11 cell lines.

hEPO and Ebola GP1 were expressed in ΔFucT6 and ΔFucT6-fut11 and glycans from purified protein from these cell cultures were released and analyzed on Capillary Electrophoresis (CE). A: hEPO, B: Ebola GP1. Square: GlcNAc, circle: mannose, triangle: α1,3-fucose. Annotations based solely on the MALDI-TOF pattern, no standards were run.

Figure 14:
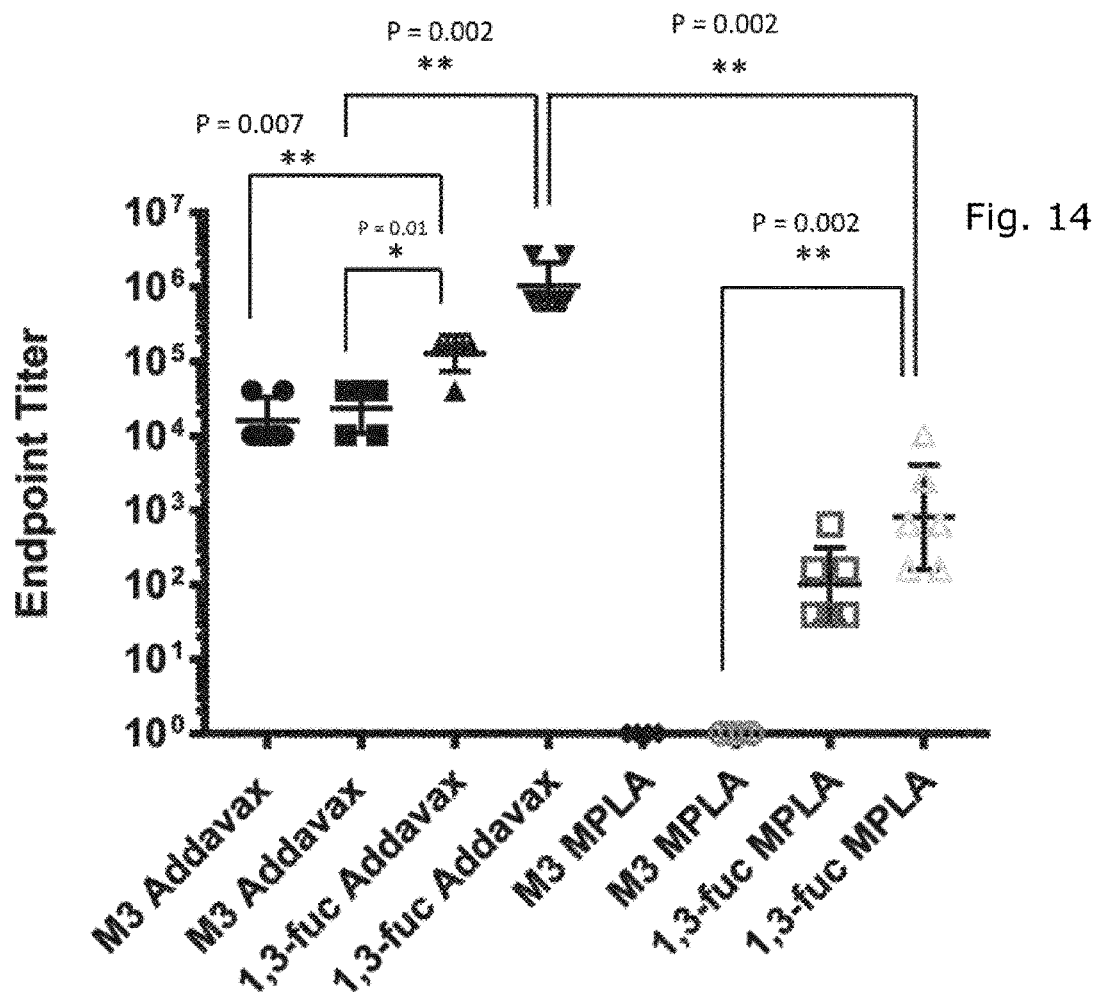

FIG. 14: VAR2CSA glycan dependent induction of antibodies against VAR2CSA.

Mice (6 per group, except Day 56 [M3]+AddaVax, which had 5 mice) were immunized three times with purified VAR2CSA expressed in and S2-VAR2CSA-fut11, formulated with either AddaVax (A) or MPLA (M). Blood samples were taken post immunization at days 14 (no detectable titers (data not shown)), 35 and 56. Total antibody titers were determined by ELISA on plates coated with S2-VAR2CSA. The horizontal line represents the geometric means per group. The statistical analysis was performed by a non-parametric, two-tailed, Mann-Whitney Rank Sum Test, with statistical significance being defined at threshold P<0.05, with cut-off calculated by (3×mean[PBS])+(3×standard deviation[PBS]). Significant differences between groups are *, P<0.05; **, P<0.01. Data for M3 AddaVax is from Example 2.

Figure 15:
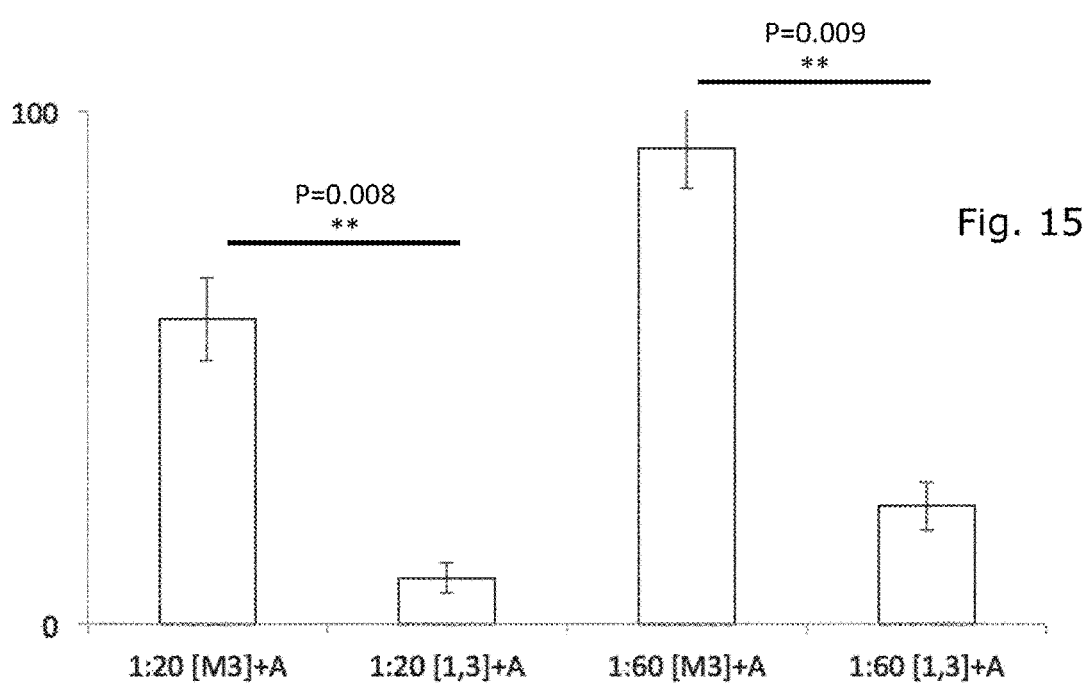

FIG. 15: Inhibition capacity of antibodies elicited by glyco-variants of ID1-ID2a on Day 56. CSA-coated wells of 96-well FACS plates were exposed to parasite IEs and diluted serum from either [M3]VAR2CSA or S2-VAR2CSA-fut11 immunized mice. After incubation, the unbound IEs were quantified. The mean percentage was calculated as ((serum sample-background)/(no serum sample-background))×100. The mean percentage of binding is shown relative to binding in wells without inhibitor. Error bars are standard deviations of triplicate reactions. The assay was performed once. The Y-axis represents binding % of IE binding to CSA. The statistical significance was determined by paired Student's t-test (normal distribution deemed valid by Q-Q plot) with significance being **, p<0.01. The data points for the control [M3]+A is from Example 2.

DETAILED DISCLOSURE OF THE INVENTION

Definitions

The term "polypeptide" is in the present context intended to mean both short peptides of from 2 to 10 amino acid residues, oligopeptides of from 11 to 100 amino acid residues, and polypeptides of more than 100 amino acid residues. Furthermore, the term is typically also intended to include proteins, i.e. functional biomolecules comprising at least one polypeptide; when comprising at least two polypeptides, these may form complexes, be covalently linked, or may be non-covalently linked. The polypeptide (s) in a protein can be glycosylated and/or lipidated and/or comprise prosthetic groups. In the present application, polypeptides and proteins are all glycosylated.

The term "subsequence" means any consecutive stretch of at least 3 amino acids or, when relevant, of at least 3 nucleotides, derived directly from a naturally occurring amino acid sequence or nucleic acid sequence, respectively.

The term "amino acid sequence" is the order in which amino acid residues, connected by peptide bonds, lie in the chain in peptides and proteins in the direction from the free N-terminus to the free C-terminus.

The term "adjuvant" or "immunological adjuvant" has its usual meaning in the art of vaccine technology, i.e. a substance or a composition of matter which is 1) not in itself capable of mounting a specific immune response against the immunogen of the vaccine, but which is 2) nevertheless capable of enhancing the immune response against the immunogen. Or, in other words, vaccination with the adjuvant alone does not provide an immune response against the immunogen, vaccination with the immunogen may or may not give rise to an immune response against the immunogen, but the combined vaccination with immunogen and immunological adjuvant induces an immune response against the immunogen which is stronger than that induced by the immunogen alone.

"Sequence identity" is in the context of the present invention determined by comparing 2 optimally aligned sequences of equal length (e.g. DNA, RNA or amino acid) according to the following formula: $(N_{ref} - N_{dif}) \cdot 100 / N_{ref}$, wherein $N_{ref}$ is the number of residues in one of the 2 sequences and $N_{dif}$ is the number of residues which are non-identical in the two sequences when they are aligned over their entire lengths and in the same direction. So, two sequences 5'-ATTCGGAAC-3' and 5'-ATACGGGAC-3' will provide the sequence identity 77.8% ($N_{ref}=9$ and $N_{dif}=2$). It will be understood that such a sequence identity determination requires that the two aligned sequences are aligned so that there are no overhangs between the two sequences: each amino acid in each sequence will have to be matched with a counterpart in the other sequence.

"An immunogenic carrier" is a molecule or moiety to which an immunogen or a hapten can be coupled in order to enhance or enable the elicitation of an immune response against the immunogen/hapten. Immunogenic carriers are in classical cases relatively large molecules (such as tetanus toxoid, KLH, diphtheria toxoid etc.) which can be fused or conjugated to an immunogen/hapten, which is not sufficiently immunogenic in its own right—typically, the immunogenic carrier is capable of eliciting a strong T-helper lymphocyte response against the combined substance constituted by the immunogen and the immunogenic carrier, and this in turn provides for improved responses against the immunogen by B-lymphocytes and cytotoxic lymphocytes. More recently, the large carrier molecules have to a certain extent been substituted by so-called promiscuous T-helper epitopes, i.e. shorter peptides that are recognized by a large fraction of HLA haplotypes in a population, and which elicit T-helper lymphocyte responses.

A "linker" is an amino acid sequence, which is introduced between two other amino acid sequences in order to separate them spatially. A linker may be "rigid", meaning that it does substantially not allow the two amino acid sequences that it connects to move freely relative to each other. Likewise, a "flexible" linker allows the two sequences connected via the linker to move substantially freely relative to each other. In fusion proteins, which are part of the present invention, both types of linkers are useful.

A "T-helper lymphocyte response" is an immune response elicited on the basis of a peptide, which is able to bind to an MHC class II molecule (e.g. an HLA class II molecule) in an antigen-presenting cell and which stimulates T-helper lymphocytes in an animal species as a consequence of T-cell receptor recognition of the complex between the peptide and the MHC Class II molecule presenting the peptide.

An "immunogen" is a substance of matter which is capable of inducing an adaptive immune response in a host, whose immune system is confronted with the immunogen. As such, immunogens are a subset of the larger genus "antigens", which are substances that can be recognized specifically by the immune system (e.g. when bound by antibodies or, alternatively, when fragments of the are antigens bound to MHC molecules are being recognized by T-cell receptors) but which are not necessarily capable of inducing immunity—an antigen is, however, always capable of eliciting immunity, meaning that a host that has an established memory immunity against the antigen will mount a specific immune response against the antigen.

A "hapten" is a small molecule, which can neither induce nor elicit an immune response, but if conjugated to an immunogenic carrier, antibodies or TCRs that recognize the hapten can be induced upon confrontation of the immune system with the hapten carrier conjugate.

An "adaptive immune response" is an immune response in response to confrontation with an antigen or immunogen, where the immune response is specific for antigenic determinants of the antigen/immunogen—examples of adaptive immune responses are induction of antigen specific antibody production or antigen specific induction/activation of T helper lymphocytes or cytotoxic lymphocytes.

A "protective, adaptive immune response" is an antigen-specific immune response induced in a subject as a reaction to immunization (artificial or natural) with an antigen, where the immune response is capable of protecting the subject against subsequent challenges with the antigen or a pathology-related agent that includes the antigen. Typically, prophylactic vaccination aims at establishing a protective adaptive immune response against one or several pathogens.

"Stimulation of the immune system" means that a substance or composition of matter exhibits a general, non-specific immunostimulatory effect. A number of adjuvants and putative adjuvants (such as certain cytokines) share the ability to stimulate the immune system. The result of using an immunostimulating agent is an increased "alertness" of the immune system meaning that simultaneous or subsequent immunization with an immunogen induces a significantly more effective immune response compared to isolated use of the immunogen.

The term "animal" is in the present context in general intended to denote an animal species (preferably mammalian), such as *Homo sapiens, Canis domesticus*, etc. and not just one single animal. However, the term also denotes a population of such an animal species, since it is important that the individuals immunized according to the method disclosed herein substantially all will mount an immune response against the immunogen of the present invention.

As used herein, the term "antibody" refers to a polypeptide or group of polypeptides composed of at least one antibody combining site. An "antibody combining site" is the three-dimensional binding space with an internal surface shape and charge distribution complementary to the features of an epitope of an antigen, which allows a binding of the antibody with the antigen. "Antibody" includes, for example, vertebrate antibodies, hybrid antibodies, chimeric antibodies, humanised antibodies, altered antibodies, univalent antibodies, Fab proteins, and single domain antibodies.

"Specific binding" denotes binding between two substances which goes beyond binding of either substance to randomly chosen substances and also goes beyond simple association between substances that tend to aggregate because they share the same overall hydrophobicity or hydrophilicity. As such, specific binding usually involves a combination of electrostatic and other interactions between two conformationally complementary areas on the two substances, meaning that the substances can "recognize" each other in a complex mixture.

The term "vector" is used to refer to a carrier nucleic acid molecule into which a heterologous nucleic acid sequence can be inserted for introduction into a cell where it can be replicated and expressed. The term further denotes certain biological vehicles useful for the same purpose, e.g. viral vectors and phage—both these infectious agents are capable of introducing a heterologous nucleic acid sequence into cells.

The term "expression vector" refers to a vector containing a nucleic acid sequence coding for at least part of a gene product capable of being transcribed. In some cases, when the transcription product is an mRNA molecule, this is in turn translated into a protein, polypeptide, or peptide.

A "glycan" is a carbohydrate or chain of carbohydrate which is linked to biomolecules (such as to lipids or proteins).

"High-mannose" in the present context denotes a Man5-Man9 glycosylation pattern.

In FIG. 3 is provided an overview of the structures and names of the glycans discussed in the present application.

Glycobiology

Glycobiology is described as the biology, biosynthesis, structure and evolution of saccharides that are widely distributed in nature and of the proteins that recognize them.

Saccharides are also called carbohydrates or sugar chains. All cells and numerous macromolecules in nature carry an array of covalently attached sugars or glycosidically linked sugar chains, which are referred to as "glycans".

Common Monosaccharide Units of Glycoconjugates

Monosaccharides have been found in hundreds of different versions in nature. However, in common glycans the monosaccharide variation is limited to the saccharides mentioned in the following table:

| Saccharides | Explanation | Example |
| --- | --- | --- |
| Pentoses | Five-carbon neutral sugars | D-xylose |
| Hexoses | Six-carbon neutral sugars | D-glucose |
| Hexosamines | Hexoses with an amino group at the 2-position, which can be either free or N-acetylated | N-acetyl-D-glucosamine |
| 6-Deoxyhexoses | | L-fucose |
| Uranic acids | Hexoses with a carboxylate group at the 6-position | D-glucoronic acid |
| Nonulosonic acids | Family of nine-carbon acidic sugars | Sialic acids |

Glycosidic Linkages

Monosaccharides are linked together via glycosidic bonds. The anomeric carbon of each saccharide is a stereocenter, which means that each glycosidic linkage can be constructed as either an α- or a β-linkage. Depending on which carbon atom in the sugar structure the binding occurs to, the name can be for example either Manα1,6 or Manα1,3, occurring on the 6$^{th}$ or the 3$^{rd}$ carbon atom respectively.

Glycan-Processing Enzymes

Generally, there are two groups of glycan-modifying enzymes the transferases and the glycosidases. The glycosyltransferases assemble branched and linear glycan chains and link monosaccharide moieties together. Glycosidases have the opposite effect; they degrade glycan structures, either for turnover of used glycans or as intermediates used as substrates in biosynthesis of glycans. The glycosyltransferases are generally specific in both donor and acceptor substrates. For example the α2,3-sialyltransferase acts on β-linked galactose and the β1,4-galactosyltransferase acts on β-linked N-acetyllucosamine (GlcNAc).

Types of Glycosylation

Glycosylation is a broad term and covers several different types of oligosaccharides and linkages. Glycosylation is found in all domains of life, and they vary greatly in structure across these domains. Bacteria have glycans on their surface. The most recognized is lipopolysaccharide (LPS) also known as "endotoxin" that is found on the surface of the outer membrane of Gram-negative bacteria. Gram-positive bacteria have capsular polysaccharide among other glycans on their cell wall. Archaea also carry glycans on the surface layer of their cell wall and they can even carry out N-glycosylation of proteins. The glycosylation in eukaryotic cells is more extensively studied and the major glycan-categories in mammalian cells are Glycosphingolipids, Proteoglycans, N-linked glycans, and O-linked glycans. See FIG. 2.

Glycolipids

Glycolipids are lipids with a glycan attached by a glycosidic bond. They are generally found on the extracellular surface of eukaryotic cell membranes. Here, they extend from the phospholipid bilayer and out into the extracellular space. Glycolipids maintain stability of the membrane and aid in cell-to-cell interactions. Furthermore, glycolipids can act as receptor for viruses and other pathogens to enter cells. Glycerolipids and sphingolipids are the two most common types of glycolipids.

Proteoglycans

Proteoglycans are heavily glycosylated proteins found on the extracellular side of animal cell membranes. Proteoglycans consists of a core protein and one or more covalently bound linear glycosaminoglycan chains. They fill out the space between cells in a multicellular organism and play significant roles in matrix assembly, modulation of cellular signals, and serve as a reservoir of biologically active small proteins such as growth factors.

O-Linked Glycosylation

The broad description of O-linked glycosylation is the attachment of a saccharide to an oxygen atom of an amino acid residue in a protein, most often serine and threonine. O-linked glycans are constructed by the addition of O—N-acetylgalactosamine, O-fucose, O-glucose, O—N-acetylglucoasmine or O-mannose. Hyper-O-glycosylation can result in the formation of mucin-type molecules that coat mucosal surfaces. Initially attached N-acetylglucosamine (mucin-type O-glycosylation) or mannose (O-mannosylation) are often prolonged (linear or branched) by 5-10 different monosaccharides, such as galactose, N-acetylglucosamine, N-galactosamine, sialic acid and xylose—see also FIG. 1. For N-acetylglucosamine based mucin-type O-glycans, eight different cores structures are known today.

N-Linked Glycosylation

It is known that the structure, number, and location of N-glycans can affect the biologic activity, protein stability, clearance rate and immunogenicity of biotherapeutic proteins. N-linked glycans are most often found on cell surfaces and on secreted proteins. The N-glycosylation on proteins can occur on the amino acid sequence of a protein where an Asn precedes any amino acid but Pro, which is in turn followed by Ser or Thr. The common N-glycan "core" structure shared between all eukaryotic cells is Manα1-3(Manα1-6)Manβ1-4GlcNAcβ1-4GlcNAcβ1-Asn-X-Ser/Thr (cf. FIG. 3). Different organisms build differently onto this core structure and the glycans are categorized into 1) "oligomannoses", where only mannose residues extend the antennas; 2) "complex", where initially GlcNAcs extend the core; 3) "hybrid", where Man extends the Manα1-6 arm of the core and GlcNAc extends the Manα1-3 arm. (cf. FIG. 3).

N-Linked Glycan Nomenclature in this Application

Describing N-glycans in writing can cause some confusion. The level of necessary detail and information can vary between situations. Sometimes it is necessary to know each branching and linkage type, and sometimes it is only necessary to communicate whether a structure has e.g. four or five mannoses. There has been no consensus up until recently, and authors have either invented their own nomenclature or modified an existing one. To avoid confusion, the present application will use the "Oxford notation", which is based on building up N-glycan structures. Therefore, it can be used to denote very complex glycans. In brief, the notation is as follows:

All N-glycans have two core GlcNAcs; F at the start of the abbreviation indicates a core fucose; Mx, number (x) of mannose on core GlcNAcs; Ax, number of antenna (GlcNAc) on trimannosyl core; "A2", biantennary with both GlcNAcs as alpha1-2 linked; Gx, number (x) of linked galactose on antenna; [3]G1 and [6]G1 indicates that the galactose is on the antenna of the alpha1-3 or alpha1-6 mannose; Sx, number (x) of sialicacids linked to galactose.

Examples of the most commonly occurring N-linked glycans in this application is given in FIG. 4.

The Oxford nomenclature is relatively intuitive. The "core" consists of two GlcNAc residues and three mannose residues. The first GlcNAc is linked to the Asn amino acid by a β-linkage. The next GlcNAc is linked by β1,4-linkage to a mannose, followed by a β1,4-linked mannose. From here, the glycan structure branches and the two remaining mannoses are attached by either an α1,3-linkage or an α1,6-linkage. This core is ubiquitous in N-glycans and is named "M3". If it has a core fucose it is called "FM3". If the position is known, then it is written in parenthesis e.g. "F(6)M3" in the case where the fucose is α1,6-linked, "F(3)M3" in the case where the core fucose is α1,3-linked, or e.g. "F(3)F(6) M3" in the case where the core has both a α1,3-linked and a α1,6-linked fucose. Once the sugars are added to this core, the name depends on these. The core with one GlcNAc is called "A1". If the position is known, then it is added in square brackets, e.g. "A1[3]" if the GlcNAc is on the α1,3-linked mannose branch. If the glycans fall into the "high-mannose" category, then some structures are "fixed" both structurally and nomenclature-wise, like "M5" and for others like "M6" the position of the added mannose residue can vary. There are names for complex tri- and tetra-antennary structures, where every linkage and position is defined. An example of a more complex structure is the "A2G(4)2S(3)1", where the "A2" describes the two β1,2-linked GlcNAcs, the "G(4)2" describes the 2 galactoses that are both β1,4-linked (and not e.g. α1,3-linked), and the "S(3)1" describes one sialic acid linked by a α2,3-link. If the position was known, then it would be indicated with a "[3]" or "[6]" referring to the α1,3- or α1,6-linked mannose branch.

N-Glycan Synthesis

The category of N-glycan that is found on a protein depends on the organism, from which it originates. All N-glycans, whether in yeast, insect cells or mammalian cells, start out as the same structure in the endoplasmic reticulum lumen. N-glycan synthesis occurs in two steps. 1) Synthesis and transfer of a dolichol-linked precursor and 2) processing steps of the Glc3Man9GlcNAc2Asn glycan.

Synthesis and Transfer of the Dolichol-Linked Precursor

The first part of N-glycosylation of a protein is the construction of the Dolichol-precursor and the attachment of this to an asparagine residue of the protein. This is described in detail below.

Dolichol phosphate is located on the cytoplasmic side of the membrane of the endoplasmic reticulum (ER). Dolichol phosphate receives GlcNAc-1-P from UDP-GlcNAc to make Dol-P-P-GlcNAc, which is then extended to Dol-P-P-M5. At this point an enzyme called "flippase" flips the structure to the inside of the ER lumen and four Man residues from Dol-P-Man and three Glc residues from Dol-P-Glc are added. This oligosaccharide is transferred to the Asn residue of a protein within the sequon N-X-S/T by an oligosaccharyltransferase that covalently binds the glycan to the protein. See FIG. 5.

Processing Steps of the M9Glc3 Glycan

Once the protein is equipped with the M9Glc3 glycan at the N-glycan sites, the processing starts. Common for most eukaryotic organisms is that the protein is folded and transported to the Golgi apparatus for further N-linked glycan processing. Depending on the organism there are different pathways and enzymes responsible for the final N-linked glycan structure. The initial de-glucosylation is carried out by α-glucosidase I, which removes the first α1,2-linked glucose residue. The next glucose is α1,3-linked and removed by α-glucosidase II. After removal of these two glucose residues the N-linked glycan processing pathway intersects with the protein quality control pathway to ensure proper folding of the newly synthesized proteins carrying M9Glc1. The quality control pathway is mainly mediated by the ER chaperones calnexin and calreticulin. These two chaperones require the presence of the α1,3-linked glucose residue to bind to the protein. As soon the last glucose residue is removed, the chaperones terminate their folding process. This step leaves either a correctly or incorrectly folded protein with M9. The incorrectly folded proteins are re-glucosylated by a glucosyltransferase resulting in a monoglucosylated form that can again bind to chaperones. If proper folding ultimately fails the protein is degraded in a separate ER compartment, the ER-associated degradation pathway (ERAD). Correctly folded glycoproteins are finally processed by a class I α-mannosidase which removes the α1,2-mannose on the B-branch. Now, the glycoprotein, which carries M8, is transported to the Golgi where the remaining glyco-processing takes place. The proteins are delivered to the cis-side of the Golgi and are modified as they move through the medial to the trans Golgi cisternae. The pathway from now on depends on whether the N-linked glycosylation is taking place in yeast, plants, insects or mammals (FIG. 6).

This is where N-linked glycans are split up in "oligomannose", "complex", or "hybrid" as described in FIG. 3. Biosynthesis of complex and hybrid N-linked glycans is initiated in the medial-Golgi N-acetylglucosaminyltransferase I (GlcNAcT I), which adds GlcNAc to the second carbon atom of the α1,3-Man in the core or M5. Next, the two mannoses on the 6-branch are cleaved off by α-mannosidase II to yield A1. α-mannosidase II can only act after the action of GlcNAcT I, as it is substrate specific for A1M5. The resulting A1 is the point where invertebrates and plants start separating from mammals. The genome of plants and invertebrates, including insects, encodes a hexoaminidase by the fused lobes gene (fdl) that removes the terminal GlcNAc residue and forms M3. In contrast, the mammalian cells encode N-aetylglucosaminyltransferase II (GlcNAcT II) that adds a GlcNAc on the 6-branch and thus forms A2. This structure is then further extended to contain galactose and sialic acids. See FIG. 6. For some mammalian glycoproteins tri- or tetra-antennary structures are also found. The major core modification in both mammalian, invertebrate and plant glycans is the attachment of core fucose. In plants and some insect cells, core fucose is often added by a α1,3-linkage and in other insect cells and mammalian cells it is added by a α1,6-linkage. Similar to α-mannosidase II, α1,6-fucosyltransferase also requires the preceding action of GlcNAcT I to function. In plants, the addition of β1,2-xylose to the β-Man of the core is also common.

The following abbreviations are used throughout the present application:

α-gal: galactose-α1,3-galactose
BEVS: Baculovirus Expression Vector System
BHK21: Baby Hamster Kidney Cell
Cas9: CRISPR Associated protein 9
CE: Capillary Electrophoresis
CHO: Chinese Hamster Ovary Cells
CLR: C-type Lectin Receptor
ConA: Concanavalin A
CRISPR: Clustered Regularly Interspaced Short Palindromic Repeats
DC: Dendritic Cell
DC-SIGN: Dendritic Cell Specific Intercellular adhesion molecule-3-Grabbing Non-integrin
Ebola GP1: Ebola Glycoprotein 1
ESI: Electron spray ionization FAB: Fast atom bombardment
Fab: Antigen binding fragment (of antibodies)
Fc: Constant fragment (of antibodies)
fdl: fused lobes gene
FucT6: α1,6-fucosylatransferase gene
fut11: α1,3-fucosylatransferase gene
GalNAc: N-acetylgalactosamine
GlcNAc: N-acetylglucosamine
GlcNAcT I: N-acetylglucosaminyl transferase I gene
GlcNAcT II: N-acetylglucosaminyl transferase II gene
HA: hemagglutinin
hEPO: human erythropoietin
HER2: Human epidermal growth factor receptor 2
HILIC: Hydrophilic interaction chromatography
HM: High-mannose
ID1-ID2a: Interdomain 1—Interdomain 2a (of VAR2CSA).
Indel: Insert/deletion
LC-MS: Liquid Chromatography Mass Spectrometry
LCA: *Lens culinaris* agglutinin
LPS: Lipopolysaccharide
M3 (or "Man$_3$"): refers to the "core" structure of glycans
mAb: monoclonal antibody
MALDI-TOF: Matrix-assisted laser desorption/ionization Time of Flight
MGAT4: N-acetylglucosaminyl transferase IV gene
MGAT5: N-acetylglucosaminyl transferase V gene
MHC: Major histocompatibilty complex
mo-DC: monocyte derived dendritic cell
MPLA: Monophosphoryl lipid A
MR: Mannose receptor
MS: Mass spectrometry
Neu5Gc: N-glycolylneuraminic acid
NHEJ: Non-homologous end joining
PAM: Protospacer Adjacent Motifs
PM: Placental Malaria
PRR: Pattern recognition receptors
PTM: Post-translational modification
QIT: Quadrupole Ion Trap
S2: *Drosophila melanogaster* Schneider 2 cells
S3: *Drosophila melanogaster* Schneider 3 cells
SDS-PAGE: sodium dodecyl sulfate polyacrylamide gel electrophoresis
SPR: Surface Plasmon Resonance
TLR: Toll-like Receptor
VAR2CSA: Receptor of malaria infected erythrocytes, which bind to placenta cells
VLP: Virus-like particle
WT: Wild-type

SPECIFIC EMBODIMENTS OF THE INVENTION

General Findings Leading to the Invention

An S2 cell line was engineered to display high-mannose glycans in >75% of secretome glycans and the immunological effects of high-mannose glycan structures were evaluated. In vivo in mice, antibodies from VAR2CSA carrying high-mannose glycans were found to appear at similar levels as the wild type. However, the antibodies raised against antigens carrying high-mannose glycan structures performed significantly better in a malaria parasite inhibition assay. In vitro it was further found that dendritic cells reacted differently to pauci-mannose vs. high-mannose. Finally, additional cell lines were constructed to evaluate the immunological effects of adding α1,3-fucose to VAR2CSA. Remarkably, VAR2CSA engineered to carry α1,3-fucose exhibited a significant increase in the total elicited number of IgG in mice. Furthermore, these antibodies were also superior in inhibiting binding of malaria parasite infected erythrocytes to CSA.

With the aim of producing high-mannose (M5-M9) glycan structures, the golgi α-Mannosidase Ia gene was disrupted in engineered S2 cell lines, and this provided a marked shift from mostly M3 and FM3 (>77%) in the WT to 75-87% H5-H9 for three monoclonal α-Mannosidase Ia deleted cell lines. Using this newly constructed "high-mannose cell line", two vaccine antigens were produced and their high-mannose glycan structures were confirmed. Both ID1-ID2a and HER2 were shown to carry more than 75% high-mannose structures. Immunizations in mice revealed equal antibody levels between glyco-engineered antigens carrying high-mannose structures compared with antigen carrying wild-type pauci-mannose glycan structures. Remarkably, the functionality of antibodies was significantly higher for ID1-ID2a carrying high-mannose compared with ID1-ID2a carrying pauci-mannose structures. This was shown in a parasite inhibition assay for both soluble antigen formulated with the adjuvant AddaVax and antigen coupled to VLPs. Besides the fact that ID1-ID2a carrying high-mannose raised more functional antibodies than ID1-ID2a carrying pauci-mannose glycan structures, there was also a significant effect from soluble antigen formulated with an adjuvant compared with antigen coupled to a VLP.

It has been shown several times that the difference between antigens carrying mannose and "naked" antigens makes a noteworthy difference on the immune response. However, the difference between pauci-mannose and high-mannose on an antigen has never been studied in depth.

The apparent polarization of the immune response in functionality between ID1-DI2a carrying high-mannose glycans and ID1-ID2a carrying pauci-mannose glycans was then investigated. Subjecting glyco-engineered ID1-ID2a and HER2 vaccine antigens to various DC assays it was found that pauci-mannose has higher binding rate to DCs than high-mannose. Moreover, activation marker expression on mo-DC surfaces was measured following LPS induction and glyco-engineered antigen exposure.

Also the immunogenic, and potentially allergenic, α1,3-linked fucose was added to glycan structures, first on hEPO and Ebola GP1 as model proteins, and subsequently on the VAR2CSA placental malaria antigen. Mice were then immunized with this glyco-engineered VAR2CSA, which provided for a significant increase in total antibody level. Remarkably, even the level of raised antibodies after two immunizations with VAR2CSA carrying α1,3-linked fucose was significantly higher than antibody level after three immunizations with ID1-ID2a carrying α1,6-linked fucose. Further, when these antibodies were compared for functionality in a parasite inhibition assay the antibodies elicited by VAR2CSa carrying α1,3-linked fucose were significantly better at inhibiting binding of IEs to CSA than antibodies elicited by ID1-ID2a carrying α1,6-linked fucose.

Embodiments of the 1$^{st}$ Aspect of the Invention

The non-plant polypeptide or protein comprising N-linked glycans that comprise α1,3-linked fucose, which constitutes the 1$^{st}$ aspect of the invention is, as shown herein, particularly useful as vaccine agents when compared to antigens carrying α1,6-linked fucose. In particular, "high-mannose" glycan versions of these antigens are useful, i.e.

those versions that include increased proportions of Man5-Man9 structures compared to the naturally occurring expression product.

Hence, in important embodiments, the polypeptide or protein comprises F(3)M3 and F(3)F(6)M3 glycan structures (cf. the discussion of N-linked glycan structure nomenclature herein). Typically, the polypeptide or protein will be one which is important as a target for active immunization, meaning that the polypeptide or protein is of mammalian (which is typical for cancer antigens), crustacean (certain crustaceans or their expression products cause disease, in particular in fish), insect, arachnoid, viral, bacterial, helminthic, or protozoan origin.

In particular, the polypeptide or protein of the 1$^{st}$ aspect is an antigen against which it is desirable to vaccinate. Non-limiting examples are the model antigens disclosed herein (VAR2CA, HER2), but any protein or peptide derived from disease provoking or disease causing agents is of relevance. Further preferred proteins are selected from a viral protein or polypeptide from HIV, Ebola virus, Zika virus, Chikungunya virus, Dengue virus, Hepatitis A virus, influenza virus, Polio virus, Rabies virus, Measles virus, mumps virus, rubella virus, Rotavirus virus, Smallpox virus, Chickenpox virus, Hepatitis B virus, human papillomavirus, varicella zoster virus, and Yellow fever virus; and a bacterial protein or polypeptide from *Clostridium tetanii, Corynebacterium diphtheria, Haemophilus influenzae, Bordetella pertussis, Streptococcus pneumoniae,* and *Neisseria meningitides*. As mentioned herein, these proteins and polypeptides are all associated with diseases and the provision of the proteins and polypeptides of the invention hence also provides the possibility of treating or reducing the risk of developing the diseases associated with the wild-type of the proteins and polypeptides.

The polypeptide or protein can as shown herein be obtained by a method comprising expressing polynucleotide(s) encoding the relevant polypeptide or protein in an S2 cell (or other suitable cell) genetically modified so as to produce an active α1,3-fucosyltransferase. Cell lines useful for this purpose are the S2 cell lines ΔFucT6-fut11 or S2-fut11 disclosed in detail below.

A particularly interesting embodiment of the first aspect of the invention is a protein or polypeptide wherein at least at least 25% of individual protein/peptide species comprise α1,3-linked fucose (and preferably high mannose glycans), such as at least 30%, at least 35%, at least 40%, at least 45%, at least 50%, at least 55%, at least 60%, at least 65%, at least 70%, and at least 75%. This is to mean that the glycosylation pattern naturally varies from molecule to molecule having the same amino acid sequence, but that the preferred polypeptide or protein of the present invention is one where the α1,3-linked fucose (and preferably high mannose glycans) appear in a large proportion of the molecules having the same amino acid sequences. As shown herein, it is possible by employing the methods and cells of the invention to produce proteins and polypeptides where >75% of the molecular species of each polypeptide/protein comprise α1,3-linked fucose and/or high mannose glycans.

In some embodiments, the polypeptide or protein further comprises or is coupled via a non-peptide bond to a heterologous moiety, such as a purification tag, an immunogenic carrier molecule or T-helper lymphocyte epitope, a solubility-modifying group, a protraction group, a targeting moiety, a virus-like particle, and an immune modulating moiety, said heterologous moiety optionally being fused to the polypeptide or protein via a peptide linker. Such a heterologous moiety imparts a further functionality to the polypeptide or protein: increased immunogenicity, ease of purification, increased biological half-life etc. In some cases it is practical to use a "linker" (rigid or flexible as the need may dictate), i.e. a relatively short stretch of amino acids instead of coupling the moiety directly to the protein/polypeptide—this can e.g. be the case in order to avoid steric interactions between the moiety and the protein/polypeptide.

Expression Systems

Numerous expression systems exist that comprise at least a part or all of the compositions discussed above. Eukaryote-based systems can be employed for use with the present invention to produce N-glycosylated polypeptides, proteins and peptides. Many such systems are commercially and widely available.

The insect cell/baculovirus system can produce a high level of protein expression of a heterologous nucleic acid segment, such as described in U.S. Pat. Nos. 5,871,986, 4,879,236, both herein incorporated by reference, and which can be bought, for example, under the name MAXBAC® 2.0 from INVITROGEN® and BACPACK™ Baculovirus expression system from CLONTECH®

In addition to the disclosed expression systems disclosed herein, other examples of expression systems include STRATAGENE®'s COMPLETE CONTROL™ Inducible Mammalian Expression System, which involves a synthetic ecdysone-inducible receptor. Another example of an inducible expression system is available from INVITROGEN®, which carries the T-REX™ (tetracycline-regulated expression) System, an inducible mammalian expression system that uses the full-length CMV promoter. INVITROGEN® also provides a yeast expression system called the *Pichia methanolica* Expression System, which is designed for high-level production of recombinant proteins in the methylotrophic yeast *Pichia methanolica*. One of skill in the art would know how to express a vector, such as an expression construct, to produce a nucleic acid sequence or its cognate polypeptide, protein, or peptide.

2$^{nd}$ Embodiment of the Invention: Compositions of the Invention; Vaccines

Immunogenic compositions, in particular vaccines, according to the invention may be prophylactic (i.e. suited to prevent infection) or therapeutic (i.e. to treat disease after infection) or they may be useful for induction of antibody production in animals used for that purpose.

The immunogenic composition of the invention comprises a polypeptide or protein according to the first aspect of the invention (or a polypeptide or protein produced according to the method of the 5$^{th}$ aspect of the invention) in admixture with at least one immunological adjuvant and optionally a pharmaceutically acceptable carrier and/or diluent and/or excipient; see below for the detailed discussion of immunological adjuvants and other substances in the composition.

Typically, an immunogenic composition of the invention is in the form of a liquid formulation (suitable for injection or ingestion) such as a solution, a suspension, an emulsion, or a suspoemulsion, or in the form of a solid or semisolid formulation, such as a powder, tablet, suppository, pill, gel, cream, or ointment. Conveniently, an immunogenic composition of the invention is contained a unit dose form, such as in freeze-dried form.

Vaccines disclosed herein typically comprise immunising N-glycosylated polypeptide(s), protein(s) or peptide(s), usually in combination with "pharmaceutically acceptable carriers", which include any carrier that does not itself induce the production of antibodies harmful to the individual receiving the composition or targeting the protein/pathogen. Suitable carriers are typically large, slowly metabolized macromolecules such as proteins, polysaccharides, polylactic acids, polyglycolic acids, polymeric amino acids, amino acid copolymers, lipid aggregates (such as oil droplets or liposomes), and inactive virus particles.

Such carriers are well known to those of ordinary skill in the art. Additionally, these carriers may function as immunostimulating agents ("adjuvants"). Furthermore, the antigen or immunogen may be conjugated to a bacterial toxoid, such as a toxoid from diphtheria, tetanus, cholera, H. pylori, etc. pathogen, cf. the description of immunogenic carriers supra.

The pharmaceutical compositions disclosed herein thus typically contain an immunological adjuvant, which is commonly an aluminium based adjuvant (including an aluminium salt), an oil-in-water emulsion, a saponin, complete and incomplete Freund's adjuvant, and a cytokine; or one of the other adjuvants described in the following:

Preferred adjuvants to enhance effectiveness of the composition include, but are not limited to:
(1) aluminium salts (alum), such as aluminium hydroxide, aluminium phosphate, aluminium sulfate, etc;
(2) oil-in-water emulsion formulations (with or without other specific immunostimulating agents such as muramyl peptides (see below) or bacterial cell wall components), such as for example (a) MF59 (WO 90/14837; Chapter 10 in Vaccine design: the subunit and adjuvant approach, eds. Powell & Newman, Plenum Press 1995), containing 5% Squalene, 0.5% Tween 80, and 0.5% Span 85 (optionally containing various amounts of MTP-PE (see below), although not required) formulated into submicron particles using a microfluidizer such as Model 110Y microfluidizer (Microfluidics, Newton, MA), (b) SAF, containing 10% Squalane, 0.4% Tween 80, 5% pluronic-blocked polymer L121, and thr-MDP (see below) either microfluidized into a submicron emulsion or vortexed to generate a larger particle size emulsion, (c) AddaVax™ (a squalene-based oil-in-water nano-emulsion similar to MF59, and (d) Ribi adjuvant system (RAS), (Ribi Immunochem, Hamilton, MT) containing 2% Squalene, 0.2% Tween 80, and one or more bacterial cell wall components from the group consisting of monophosphoryl lipid A (MPL), trehalose dimycolate (TDM), and cell wall skeleton (CWS), preferably MPL+CWS (Detox™);
(3) saponin adjuvants such as Stimulon™ (Cambridge Bioscience, Worcester, MA) may be used or particles generated therefrom such as ISCOMs (immunostimulating complexes);
(4) Complete Freund's Adjuvant (CFA) and Incomplete Freund's Adjuvant (IFA);
(5) cytokines, such as interleukins (eg. IL-1, IL-2, IL-4, IL-5, IL-6, IL-7, IL-12, etc.), interferons (e.g. gamma interferon), macrophage colony stimulating factor (M-CSF), tumor necrosis factor (TNF), etc.; and
(6) other substances that act as immunostimulating agents to enhance the effectiveness of the composition. Alum, MF59™, and Addavax™ adjuvants are preferred, but MPLS/LPS and TLR4 agonists are other possibilities.

Muramyl peptides include, but are not limited to, N-acetyl-muramyl-L-threonyl-D-isoglutamine (thr-MDP), N-acetyl-normuramyl-L-alanyl-D-isoglutamine (nor-MDP), N-acetylmuramyl-L-alanyl-D-isoglutaminyl-L-alanine-2"-2'-dipalmitoyl-sn-glycero-3-hydroxyphosphoryloxy)-ethylamine (MTP-PE), etc.

The immunogenic compositions (e.g. the immunising antigen or immunogen or polypeptide or protein or nucleic acid, pharmaceutically acceptable carrier, and adjuvant) typically will contain diluents, such as water, saline, glycerol, ethanol, etc. Additionally, auxiliary substances, such as wetting or emulsifying agents, pH buffering substances, and the like, may be present in such vehicles.

Typically, the immunogenic compositions are prepared as injectables, either as liquid solutions or suspensions; solid forms suitable for solution in, or suspension in, liquid vehicles prior to injection may also be prepared. The preparation also may be emulsified or encapsulated in liposomes for enhanced adjuvant effect, as discussed above under pharmaceutically acceptable carriers.

Immunogenic compositions used as vaccines comprise an immunologically effective amount of the antigenic or immunogenic polypeptides, as well as any other of the above-mentioned components, as needed. By "immunologically effective amount", it is meant that the administration of that amount to an individual, either in a single dose or as part of a series, is effective for treatment or prevention. This amount varies depending upon the health and physical condition of the individual to be treated, the taxonomic group of individuals to be treated (eg. nonhuman primate, primate, etc.), the capacity of the individual's immune system to synthesize antibodies or generally mount an immune response, the degree of protection desired, the formulation of the vaccine, the treating doctor's assessment of the medical situation, and other relevant factors. It is expected that the amount will fall in a relatively broad range that can be determined through routine trials. However, for the purposes of protein vaccination, the amount administered per immunization is typically in the range between 0.5 µg and 500 mg (however, often not higher than 5,000 µg), and very often in the range between 10 and 200 µg.

The immunogenic compositions are conventionally administered parenterally, eg, by injection, either subcutaneously, intramuscularly, or transdermally/transcutaneously (e.g. as in WO 98/20734). Additional formulations suitable for other modes of administration include oral, pulmonary and nasal formulations, suppositories, and transdermal applications.

Dosage treatment may be a single dose schedule or a multiple dose schedule. The vaccine may be administered in conjunction with other immunoregulatory agents.

3$^{rd}$ Aspect of the Invention: Methods of Prophylaxis/Treatment or Antibody Induction/Production Disclosed Herein As mentioned above, the proteins and polypeptides of the first aspect of the invention enables the method of the 3$^{rd}$ aspect for inducing/enhancing a specific immune response in an animal, such as a human being, the method comprising at least one immunization of the animal with an effective amount of the protein or polypeptide of the first aspect or with the composition of the 2$^{nd}$ aspect.

Irrespective of the precise protein or polypeptide, it is preferred to administer the active principle in both a priming immunization and at least one subsequent booster immunization. Alternatively, the somewhat more recent approach of utilising cluster immunizations (i.e. an immunization scheme where repeated dosages of the immunogen(s) are administered at short intervals in the beginning of the immunization regimen before a memory immune response has been established; this is then followed by delay immunizations that resemble the traditional booster immunization used in a prime-boost immunization regimen).

The disease targeted by immunization naturally depends on the origin of the immunogen. For instance, in some embodiments of the present invention the at least one immunization reduces risk in the vaccinated animal of attracting a disease caused by an infectious organism or where the immunization modulates an existing immune response against the protein or polypeptide—the latter is e.g. relevant when treating allergies by specific immune therapy, in which case the undesired Th2 dependent IgE immune response is modulated into an non-harmful Th1 dependent IgG immune response.

In other embodiments of the $3^{rd}$ aspect, the at least one immunization treats or ameliorates or reduces risk of disease caused by an autologous protein or by a cell producing said autologous protein. This is e.g. relevant in cancer immune therapy, where cancer-associated or cancer-specific antigens can be targeted, but also when immunizing actively against autologous proteins that in their own right contribute to progression of disease.

Immunization routes are typically selected from parenteral routes such as the subcutaneous, intradermal, subdermal, intraperitoneal, intrathecal, and intramuscular routes, or via the oral or oral mucosal routes. See below for details.

To conclude the method of the $3^{rd}$ aspect is normally selected from
a) a method for disease prophylaxis;
b) a method for treatment or amelioration of disease; and
c) a method for antibody production.

Related to the third aspect is also the protein or polypeptide of the $1^{st}$ a aspect of the invention or the composition of the second aspect for use in a prophylactic or therapeutic method of the $3^{rd}$ aspect. Likewise, a related aspect is the use of a protein or polypeptide of the first aspect for the preparation of a pharmaceutical composition (of the second aspect) for use in a therapeutic or prophylactic method of the $3^{rd}$ aspect.

The $3^{rd}$ aspect of the invention generally relates to induction of immunity and as such also entails method that relate to treatment, prophylaxis and amelioration of disease as well as to methods the aim at producing antibodies in a host animal.

When immunization methods entail that a polypeptide disclosed herein or a composition comprising such a polypeptide is administered the animal (e.g. the human) typically receives between 0.5 and 5,000 μg of the polypeptide disclosed herein per administration, cf. above.

In preferred embodiments of this aspect, the immunization scheme includes that the animal (e.g. the human) receives a priming administration and one or more booster administrations.

Preferred embodiments of this aspect disclosed herein comprise that the administration is for the purpose of inducing protective of therapeutic immunity against an infectious agent. Alternatively, the administration is aimed at preventing or treating diseases caused by autologous proteins or cells; such diseases include (malignant) neoplastic diseases but also diseases where autologous proteins induce undesirable side effects.

The compositions disclosed herein can induce humoral immunity, so the administration is in some embodiments for the purpose of inducing antibodies specific for the antigen, cell or organism from which the glycosylated polypeptide or protein is derived, and wherein said antibodies or B-lymphocytes producing said antibodies are subsequently recovered from the animal to be used in their own right as pharmaceutical, diagnostic or laboratory agents.

Pharmaceutical compositions can as mentioned above comprise polypeptides/proteins disclosed herein. The pharmaceutical compositions will comprise a therapeutically effective amount thereof.

The term "therapeutically effective amount" or "prophylactically effective amount" as used herein refers to an amount of a therapeutic agent to treat, ameliorate, or prevent a desired disease or condition, or to exhibit a detectable therapeutic or preventative effect. The effect can be detected by, for example, chemical markers or antigen levels. Therapeutic effects also include reduction in physical symptoms, such as decreased body temperature. The precise effective amount for a subject will depend upon the subject's size and health, the nature and extent of the condition, and the therapeutics or combination of therapeutics selected for administration. Thus, it is not useful to specify an exact effective amount in advance. Reference is however made to the ranges for dosages of immunologically effective amounts of polypeptides, cf. above.

However, the effective amount for a given situation can be determined by routine experimentation and is within the judgement of the clinician.

Pharmaceutically acceptable salts can be used therein, for example, mineral acid salts such as hydrochlorides, hydrobromides, phosphates, sulphates, and the like; and the salts of organic acids such as acetates, propionates, malonates, benzoates, and the like. A thorough discussion of pharmaceutically acceptable excipients is available in Remington's Pharmaceutical Sciences (Mack Pub. Co., N.J. 1991).

Pharmaceutically acceptable carriers in therapeutic compositions may contain liquids such as water, saline, glycerol and ethanol. Additionally, auxiliary substances, such as wetting or emulsifying agents, pH buffering substances, and the like, may be present in such vehicles.

Typically, the therapeutic compositions are prepared as injectables, either as liquid solutions or suspensions; solid forms suitable for solution in, or suspension in, liquid vehicles prior to injection may also be prepared. Liposomes are included within the definition of a pharmaceutically acceptable carrier.

$4^{th}$ Aspect of the Invention: Genetically Modified Cells of the Invention

Genetically modified cells disclosed herein are useful as organisms for producing proteins and polypeptides, typically proteins and polypeptides of the first aspect of the invention.

A genetically modified non-plant eukaryotic cell of the $4^{th}$ aspect is one that comprises at least one heterologous polynucleotide sequence encoding and expressing a heterologous α1,3-fucosyltransferase and/or is one wherein expression of the α-Man-Ia gene has been reduced or abolished and/or or is one wherein expression of genes encoding enzymes extending glycans beyond Man3, such as Man5 has been increased. In particular, the genetically modified non-plant eukaryotic cell is capable of producing N-glycosylated protein carrying α1,3-fucosyl groups.

In some embodiments, the genetically modified non-plant eukaryotic cell of the $4^{th}$ aspect exhibits reduced or abolished function of at least one α1,6-fucosyltransferase encoding gene. As reported in the examples, these modifications in glycosylation properties result in the provision of glycosylated expression products that have been demonstrated by the inventors to be superior immunogens—not necessarily in terms of antibody titres attained but rather in the quality of the immune response induced.

In other, equally important, embodiments the genetically modified non-plant eukaryotic cell of the invention exhibits reduced or abolished function of α-Man-Ia (or an equivalent gene), a modification which increases Man5-Man9 glycosylation. This could appear counter-intuitive, but the inventors have demonstrated that deletion of this gene has the effect that the modified cells produce Man5-Man9 rather than Man3.

While the most preferred non-plant eukaryotic cell of the $4^{th}$ aspect is an insect cell (such as a *Drosophila* S cell), the specific modifications introduced are also relevant in a range of other non-plant cell types, such as mammalian cells and fungal cells such as a yeast of filamentous fungal cells.

One particularly useful modification that can characterize a modified non-plant eukaryotic cell of the $4^{th}$ aspect is presence of a heterologous polynucleotide sequence consisting of the fuc11 gene from *Arabidobsis thaliana*, or any equivalent polynucleotide encoding a plant α1,3-fucosyltransferase; such genes encoding α1,3-fucosyltransferases can be isolated from a wide variety of host cells, and currently several thousand genes are known to encode such enzymes.

For production of protein and polypeptides, it is necessary that the genetically modified cell further expresses a (heterologous) gene encoding a polypeptide or protein, preferably one of the first aspect of the invention. Further, when the genetically modified cell of the $4^{th}$ aspect expresses such a protein or polypeptide, it has been found that a large fraction displays high-mannose glycans, i.e. it is found (and preferred) that >25% of said polypeptide or protein displays high-mannose glycans, such as >30%, >35%, >40%, >45%, >50%, >55%, >60%, >65%, >70%, and more than 75% of said polypeptide or protein.

As mentioned above, the preferred genetically modified cell of the $4^{th}$ aspect is an insect cell, preferably a *Drosophila melanogaster* cell, such as an S2 or S3, or an insect cell such as Sf9, SF21, High5, and C6-36. However, in the event the cell is mammalian, it can be a CHO or HEK cell.

Useful cells are in general discussed in the following.

Eukaryotic cells can be in the form of yeasts (such as *Saccharomyces cerevisiae*) and protozoans. Alternatively, the transformed eukaryotic cells are derived from a multicellular organism such as a fungus, an insect cell, or a mammalian cell.

For production purposes, it is advantageous that the genetically modified cell disclosed herein is stably transformed by having the nucleic acids disclosed above stably integrated into its genome, and in certain embodiments it is also preferred that the genetically modified cell secretes or carries on its surface the glycosylated polypeptide disclosed herein, since this facilitates recovery of the polypeptides produced.

As noted above, stably genetically modified cells are preferred—these i.a. allows that cell lines comprised of genetically modified cells as defined herein may be established—such cell lines are particularly preferred aspects of the invention.

It is noted that the genetically modified cell of the $4^{th}$ aspect can be established as a cell line comprising the genetically modified cell; one example of such a cell line is a clonal cell line.

Further details on cells and cell lines are presented in the following:

Techniques for recombinant gene production, introduction into a cell, and recombinant gene expression are well known in the art. Examples of such techniques are provided in references such as Ausubel, Current Protocols in Molecular Biology, John Wiley, 1987-2002, and Greene and Sambrook: "Molecular Cloning: A Laboratory Manual (Fourth Edition)", Cold Spring Harbor Laboratory Press (ISBN-10: 9781936113422).

As used herein, the terms "cell", "cell line", and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a eukaryotic cell, and it includes any transformable organism that is capable of replicating a vector or expressing a heterologous gene encoded by a vector. A host cell can, and has been, used as a recipient for vectors or viruses. A host cell may be "transfected" or "transformed," which refers to a process by which exogenous nucleic acid, such as a recombinant protein-encoding sequence, is transferred or introduced into the host cell. A genetically modified cell includes the primary subject cell and its progeny.

Host cells are in the present application derived from non-plant eukaryotes, including yeast cells, insect cells, and mammalian cells for replication of the vector or expression of part or all of the nucleic acid sequence(s). Numerous cell lines and cultures are available for use as a host cell, and they can be obtained through the American Type Culture Collection (ATCC), which is an organization that serves as an archive for living cultures and genetic materials or from other depository institutions such as Deutsche Sammlung vor Micrroorganismen und Zellkulturen (DSM). An appropriate host can be determined by one of skill in the art based on the vector backbone and the desired result. A plasmid or cosmid, for example, can be introduced into a prokaryote host cell for replication of many vectors or expression of encoded proteins.

Examples of eukaryotic host cells for replication and/or expression of a vector include HeLa, NIH3T3, Jurkat, HEK293, Cos, CHO, Saos, and PC12. Many host cells from various cell types and organisms are available and would be known to one of skill in the art. Similarly, a viral vector may be used in conjunction with a host cell, particularly one that is permissive for replication or expression of the vector.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

$5^{th}$ Aspect of the Invention—Protein Production

In the method for producing an N-glycosylated polypeptide or protein carrying α1,3-fucosyl groups described under the Summary of the Invention heading above, any of the proteins disclosed in the first aspect may be prepared, and any of the cell lines of the $4^{th}$ aspect may function as host cells. In general, the method of the $5^{th}$ aspect relies on methods generally known in the art for cell culture, recombinant expression, and protein purification.

Example 1

Establishment of S2 Cell Lines Engineered to Provide High Mannose Antigens.

Plasmid Construction

The online E-CRISP tool (www.e-crisp.org; German Cancer Research Center) was used to identify CRISPR/Cas9 sequences within the Drosophila melanogaster genome that target, FucT6 (UniProt: Q9VYV5), and α-Man-Ia (UniProt: P53624). sgRNA target sequences were selected as 20 nucleotide sequences preceding an NGG PAM sequence in the genome. The oligonucleotide pairs XX-F and XX-R were used to construct DNA fragments consisting of each targeting sequence with overhangs to enable their sub cloning into pExpreS$^2$-CRISPR (ExpreS$^2$ion Biotechnologies, Hersholm, Denmark). The sequence of each synthetic oligo is provided in the following:

| Name | Sequence of oligo |
|---|---|
| FucT6_36-F | TTCGTATCGCCGATCGAGTTGGCC (SEQ ID NO: 1) |
| FucT6_36-R | AACGGCCAACTCGATCGGCGATAC (SEQ ID NO: 2) |
| FucT6_71-F | TTCGAGTTAATTGAGACTATGCAC (SEQ ID NO: 3) |
| FucT6_71-R | AACGTGCATAGTCTCAATTAACTC (SEQ ID NO: 4) |
| FucT6_56-F | TTCGCAAGGAACGGGGCTCCGAAC (SEQ ID NO: 5) |
| FucT6_56-R | AACGTTCGGAGCCCCGTTCCTTGC (SEQ ID NO: 6) |
| alpha-Man-I_138-F | TTCGTGATCAGGCGCCGGACACAC (SEQ ID NO: 7) |
| alpha-Man-I_138-R | AACGTGTGTCCGGCGCCTGATCAC (SEQ ID NO: 8) |
| alpha-Man-I_166-F | TTCGCGCTCTGGCGGATCAGCCGC (SEQ ID NO: 9) |
| alpha-Man-I_166-R | AACGCGGCTGATCCGCCAGAGCGC (SEQ ID NO: 10) |
| alpha-Man-I_520-F | TTCGAATATCGCGAGGGTCGCGAT (SEQ ID NO: 11) |
| alpha-Man-I_520-R | AACATCGCGACCCTCGCGATATTC (SEQ ID NO: 12) |

S2 Cell Culture, Transfection, and Cloning

ExpreS$^2$ Cells (ExpreS$^2$ion Biotechnologies, Hersholm, Denmark), hereafter "S2 cells", were routinely maintained at 25° C. and 130 rpm in suspension in 125 ml shake flasks (vented cap) in culture medium EX-CELL 420 Serum-Free Medium for Insect Cells (Sigma-Aldrich, cat. Nr. 14420C, Steinheim, Germany) supplemented with 100 units/mL penicillin and 0.1 mg/mL streptomycin (Pen-Strep Solution, Biological Industries, cat. 03-031B, Cromwell, CT, USA), hereafter "culture medium". The S2 cells were counted with a CASY® Cell Counter every 3-4 days and passaged by centrifugation or dilution to $8 \times 10^6$ cells/mi.

For transfection, the S2 cells were passaged to $8 \times 10^6$ cells/mi in shake flasks in culture medium and transfected the following day, by splitting the cells to $2 \times 10^6$ cells/mi and mixing with first 50 µl ExpreS$^2$ Insect-TRx5 (ExpreS$^2$ion Biotechnologies, Hersholm, Denmark) transfection reagent and second with 12.5 µg of plasmid DNA. The transfected cells were then transferred to a 25 cm$^2$ tissue culture flask (In Vitro, Fredensborg, Denmark). A polyclonal cell line was selected herein for 21 days in culture medium supplemented with 10% fetal bovine serum (FBS) (Fischer Scientific, Roskilde, Denmark) and 1.5 mg/ml zeocin (Thermo Fisher, Hvidovre, Denmark) or 4.0 mg/ml geneticin (InvivoGen, Toulouse, France), by dilution to $1 \times 10^6$ cells/ml every 3-4 days or whenever the cells reached a density higher than $1.5 \times 10^6$ cells/mi.

Hereafter the stable cell lines were transferred to a 125 ml shake flask and passaged as described in Hjerrild K A et al. (2016), Scientific Reports 6: 30357, doi:10.1038/srep30357.

Monoclonal cell lines were obtained by limited dilution in 96 well plates (In Vitro, cat. GR-655180, Fredensborg, Denmark) using non-transfected S2 feeder cells at $0.6 \times 10^6$ cells/mi. Stably transfected polyclonal cells were seeded out at concentrations of 100 cells/mL, 30 cells/mL or 10 cells/mL. The total volume in wells was 150 µl culture medium supplemented with 10% fetal bovine serum and 1.5 mg/ml zeocin or 4.0 mg/ml geneticin. Over 2-3 weeks the 96-well plates were inspected regularly and monoclonal cell lines were identified and expanded from 96 well plates to 250 mL shake flasks (Sigma-Aldrich, cat. CLS431255, St. Louis, MO, USA).

Indel Detection by Amplicon Analysis (IDAA)

IDAA was carried out as previously described.[26] Briefly, genomic DNA was extracted using PureLink™ Genomic DNA Mini Kit (Fisher Scientific, cat. nr. K182001, Roskilde, Denmark). Primers were designed using the online prediction tool "Primer3": FucT6 (F:TTCGCAAGGAACGGGGCTCCGAAC (SEQ ID NO:6), R:GCAAGGAACGGGGCTCCGAACGTT (SEQ ID NO:13)) or α-Man-Ia (F:CAACGTTGGAGCAAAA-GATTC (SEQ ID NO:14), R:AACCACC-TACCTCTTTGACCTTC, (SEQ ID NO:15)). PCR was performed using Phusion High-Fidelity PCR kit (1×HF buffer, 0.2 mM dNTP, 0.25 U Phusion polymerase, 0.025 µM forward primer, 0.25 µM reverse primer and 0.25 µM 6-FAM 5'-labelled universal primer (Thermofisher, cat. nr. F553S, Hvidovre, Denmark)). The PCR-amplicons were analyzed by fragment length analysis (Eurofins, Glostrup, Denmark).

SDS-PAGE and Lectin Blotting

Supernatant samples were analyzed by SDS-PAGE and Western Blot analysis. Briefly, proteins were resolved by 10% SDS-PAGE and then transferred to a nitrocellulose membrane. Non-specific binding was blocked by incubating the membrane in Carbo-Free™ Blocking Solution (Vector-Labs, Cat. No. SP-5040, Burlingame, CA, USA) for 30 minutes at room temperature. Then the blot was incubated for 30 minutes in PBS with 10 µg/ml biotinylated lectin and washed in PBS+0.2% Tween 20™. The secondary antibody was HRP-conjugated Streptavidin (Fisher Scientific, Roskilde, Denmark) diluted 1:5000 for 45 min followed by a wash in PBS+0.2% Tween 20™. Novex® ECL (WP20005, Fisher Scientific, Roskilde, Denmark) was used for detection. Lectins used: for recognition of α1,6-fucose: Biotinylated *Lens culinars* (LCA); high-mannose: Biotinylated *Musa paradisiaca* (BanLec) (both from VectorLabs, Burlingame, CA, USA).

Glycoprofiling

Glycoprofiling was performed as previously described in Grav L M et al. (2015), Biotechnology Journal 10:1446-56, doi:10.1002/biot.201500027. Briefly, supernatants were filtered and proteins contained in the sample were concentrated by centrifugation using Amicon Ultra columns (Merck Millipore, Merck KGaA, Darmstadt, Germany) with 3000 Da cutoff. N-glycans from retained proteins were released and fluorescently labeled with GlycoPrep Rapid N-Glycan kit (ProZyme Inc., Hayward, CA) or GlycoWorks RapiFluor-MS N-Glycan Kit (Waters, Elstree, UK). Labeled N-glycans were analyzed by Liquid Chromatography—Mass Spectrometry (LC-MS) on a Thermo Ultimate 3000 HPLC with fluorescence detector coupled on-line to a Thermo Velos Pro Ion Trap MS. Glycan abundance was measured by integrating the areas under normalized fluorescence spectrum peaks with Xcalibur software (Thermo Fisher Scientific, Hvidovre, Denmark) giving the relative amount of the glycans. All annotated sugar structures are peaks with correct mass and at least a signal to noise value of 10:1 as calculated with Xcalibur.

Results

LC-MS Analysis of the Disruption of FucT6 or α-Man-Ia

For the experiments reported below in Example 3, a cell line that does not attach core α1,6-fucose to the glycan was constructed. In order to achieve this FucT6, which encodes an α1,6-fucosyltransferase, was disrupted. The work on disrupting the FucT6 gene was conducted in a wild type cell line (S2-WT). Three CRISPR/Cas9 sgRNA target sequences for the disruption of the FucT6 gene were constructed and transfected in parallel in S2 cells to establish stable cell lines. All supernatant proteins, or the secretome, of S2-WT and the ΔFucT6 with a polyclonal disruption were analyzed on LC-MS.

It was possible to observe an effect of the disruption on a polyclonal level: The S2-WT cell line showed approximately >64% of FM3 and <12% of M3. After disruption of the FucT6 gene, the polyclonal glycan profile shifted and showed a decrease in FM3 to <37% and an increase in M3 to >39% of the total glycans. This indicated that the disruption was successful. However, to establish a monoclonal cell line with no display of fucose a further round of sub-cloning was performed. A total of 39 ΔFucT6 clones was obtained by limited dilution. These were screened by an Indel Detection by Amplicon Analysis and a lectin blot: In this technique, the DNA is extracted and the clones are analyzed on a genetic level by Indel Detection by Amplicon Analysis (IDAA). From this, clones are selected for further screening. The next screening is done on a phenotypic level by Western Blot of supernatant using a α1,6-fucose specific lectin, *Lens Culinaris* (LCA). LCA binding and signaling suggests that clones have a disruption in the FucT6 gene.

Based on the lectin blot, two clones were chosen for LC-MS analysis, and both showed similar secretome glycan patterns with 0% fucose on the glycans upon LC-MS.

To investigate if the cells had any α1,3-fucose in the glycan pool a Western Blot was carried out on the full secretome with an α1,3-fucose specific antibody, and a α1,3-fucose positive control. No such structures were observed (data not shown). This monoclonal cell line (ΔFucT6) with a disrupted FucT6 gene could i.a. now serve the basis for the experiments in Example 3.

To construct a S2 cell that glycosylated with high-mannose N-glycan structures in order to produce immunogenic antigens α-Man-Ia was disrupted in a wild type S2 cell line. Three different target sgRNAs for CRISPR/Cas9 against α-Man-Ia were chosen (See above) and transfected in S2 cells in parallel to establishing stable cell lines. Two out of the three targets did not show any effect (data not shown), however, one target showed a shift towards higher mannose glycan structures by LC-MS analysis on a polyclonal level. This polyclonal cell line was cloned by limited dilution and the monoclonal cell lines obtained hereby were initially analyzed for genotypic indels by IDAA and by a lectin blot:

A mannose specific lectin, BanLec, which distinguishes between M3 and high-mannose, is used in the blot. This lectin binds to high-mannose structures on proteins below the size of 62 kDa and this provides a clear picture of which clones might carry the disruption.

Based on the IDAA and the lectin analysis, we analyzed 3 secretome samples on LC-MS. LC-MS analysis of three of the monoclonal cell lines confirmed the IDAA and lectin blot conclusion that α-Man-Ia was disrupted. Furthermore, LC-MS analysis provided a much more detailed picture of the distribution of what we refer to as "high-mannose". The WT carried >77% FM3/M3 and <23% high-mannose, while for Δα-Man-Ia Clone A, B, and C there is a significant shift to structures of "high-mannose" character, where these represent approximately 87%, 75%, and 85% for Clone A, B, and C respectively. However, there is a small amount of FM3/M3 remaining in all three clones. It is interesting to note that the ratio between the high-mannose structures vary within the clones. Clone A and C have around 30% M8, whereas Clone B only shows around 17% M8. These three cell lines now enable production of recombinant proteins with high-mannose glycan structures in S2 cells.

Discussion

The objective of this Example was to modify the N-glycosylation in S2 cells, initially to enable studies the effect of glycosylation on vaccine immunogenicity, serum half-life, and pharmacokinetics. By disruption of the FucT6 gene, cell lines lacking core fucosylation were provided. Also, by disruption of the α-Man-Ia gene, a cell line was constructed that glycosylates with a more immunogenic pattern for production of vaccine antigens.

The disruption of neither FucT6 nor α-Man-Ia has previously been described in S2 or other insect cells. In this study the disruption of α-Man-Ia in S2 cells resulted in clones with >75% high-mannose glycans. However, in all three obtained and LC-MS analyzed clones there were still significant levels of FM3 and M3. It is advantageous with a uniform glycan pattern and the next step towards this is to disrupt other mannosidases. Our data support the fact that α-man-Ia plays an important role in trimming down the high-mannose structures to M3, although it is not the only enzyme responsible such trimming. Mammalian cells have several mannosidases and a search in the *Drosophila* genome reveals at least four other potential mannosidase targets that could be disrupted, too. Even with significant future opportunities for further glyco-engineering, the "high-mannose" cell lines established in this work can already now be applied to the expression of recombinant antigens where a high-mannose glycan pattern is desired, such as HIV or other vaccine antigens.

In summary, a cell line that glycosylate with a "high-mannose" pattern was successfully established, and this novel cell line can used for expression of vaccine antigens. Also, cell lines lacking core fucosylation were provided.

Example 2

Establishment of S2 Cell Lines Engineered to Provide High Mannose Versions of the Antigens ID1-ID2a and Her2.

Design, Expression and Purification of ID1-ID2a-SpyT and the HER2-SpyC Antigen

The ID1-ID2a (GenBank Accession no. ANG83526.1) was designed with a C-terminal BiiP secretion signal (MKL-CILLAVVAFVGLSLGG (SEQ ID NO:16)) and KOZAK (gccacc) and with N-terminal V5-tag (GKPIPNPLLGLDST (SEQ ID NO:17)), a 6×HIS-tag, and the SpyTag (AHIVMV-DAYKPTK (SEQ ID NO:18)). The final sequence was optimized for expression in *Drosophila melanogaster* S2 cells and subcloned into pExpreS$^2$-1 using EcoRI and XbaI. The construct was transfected into either S2-WT or the polyclonal Δα-Man-Ia (cf. Example 1) and selected as described previously in Hjerrild K A et al (2016) referenced supra.

The SpyCatcher-HER2 (HER2) was designed and produced as described in Palladini A. et al. (2018) OncoImmunology 7(3), e1408749, and subcloned into pExpreS$^2$-1 using XhoI and NotI. The final construct was optimized for expression in *Drosophila* and transfected stably into S2-WT or the polyclonal Δα-Man-Ia (cf. Example 1) and selected as described previously in Hjerrild K A et al. 2016. Briefly, the cells were selected over a three-week period in EX-CELL 420 insect cell medium (Sigma) supplemented with 10% FBS and 1000 µg/ml Zeocin (Invivogen). Hereafter, the cells were expanded in EX-CELL 420 and harvesting was done by centrifugation and filtrations three days after the final split. Recombinant ID1-ID2a was purified on a Ni2C sepharose column and eluted with 200 mM Imidazole.

Design, Expression and Purification of Spy-AP205 Virus-Like Particles, Hepatitis B, and Human Papilloma Virus Production of the *Acinetobacter phage*, AP205, was done as previously described in Thrane, S. et al. (2016), *Journal of Nanobiotechnology* 14:30, DOI 10.1186/s12951-016-0181-1.

In brief, the SpyCatcher (MVDTLSGLSS EQGQSGDMTI EEDSATHIKF SKRDEDGKEL AGAT-MELRDS SGKTISTWIS DGQVKDFYLY PGKYTFVETA APDGYEVATA ITFTVNEQGQ VTVNGKATKG DAHI (SEQ ID NO:19)) or SpyTag (AHIVMVDAYK PTK (SEQ ID NO:18)) peptide sequences were fused to both the N- and C-terminus of the gene encoding the AP205 coat protein (Gene ID: 956335). A flexible linker (GSGTAGGGSGS (SEQ ID NO:20), N-terminus and GTASGGSGGSG (SEQ ID NO:21), C-terminus) was used to separate each Spy-Catcher from the coat protein. The SPyCatcher VLP was expressed in *Escherichia coli* One Shot! BL21 Star™ (DE3) cells (Thermo Scientific) and purified by density gradient ultracentrifugation using an Optiprep™ step gradient (23, 29 and 35%) (Sigma). MS2 and Hepatitis B VLPs were made as previously described in Shishovs, M. et al. (2016), *J. Mol. Biol.* 428, 4267-4279 and Holmes, K. et al. (2015), *J. Biol. Chem.* 290, 16238-16245.

Analysis of N-Linked Glycans

Glycoprofiling was performed as described in Grav L. M. et al. (2015), see Example 1. Briefly, harvest supernatants were sterile filtered and proteins were concentrated by centrifugation using Amicon Ultra columns (Merck Millipore, Merck KGaA, Darmstadt, Germany) with a 3 kDa cutoff. N-glycans from retained proteins were released and fluorescently labeled with GlycoWorks RapiFluor-MS N-Glycan Kit (Waters, Elstree, UK). Labeled N-glycans were analyzed by LC-MS on a Thermo Ultimate 3000 HPLC with fluorescence detector coupled on-line to a Thermo Velos Pro Ion Trap MS. Glycan presence was measured by integrating areas under normalized fluorescence spectrum peaks with Xcalibur software (Thermo Fisher Scientific, Hvidovre, Denmark), which yielded relative amounts of the glycans. All annotated sugar structures are peaks with correct mass and at least a signal to noise value of 10:1 as calculated with Xcalibur.

Coupling to VLPs

Attachment of vaccine antigens to the AP205 VLPs was done by mixing the two in a 1:2 M ratio (ID1-ID2a-SPyT: AP205SpyC or HER2SpyC:AP205SpyT) and incubated at room temperature for 2 hours. Ultra-centrifugation was performed using an Optiprep™ step gradient (23, 29, and 35%) (Sigma). The coupled Antigen:VLP were dialyzed in 1×PBS ON at 4° C. Endotoxins were removed by addition of 1:1000 Triton 114× at 4° C. for 5 min, then 36° C. for 5 min and centrifuged at 8000×G for 1 minute, and repeated again. Hereafter the couplings were dialyzed 1×PBS ON at 4° C. and snap-freezed in liquid nitrogen and stored at −80° C. Endotoxin levels were evaluated by Pierce LAL kit (ThermoFisher).

Immunization of Mice

Female 6-8 week old BALB/c mice were immunized intramuscularly with formulated vaccines of either 1) [M3] ID1-ID2a or [HM]ID1-ID2a coupled to AP205 VLPs or with AddaVax (Invivogen) or 2) [M3]HER2 vs [HM]HER2, both coupled to VLPs and formulated with AddaVax. The mice were immunized on Day 0, 21, and 42 and blood samples were collected on Day 14, 35 and 56 and serum was frozen at −20° C.

Antibody Response Measured by Standard ELISA

Measurements of serum immunoglobulin G (IgG) levels were done by standard enzyme-linked immunosorbent assay (ELISA) as previously described in Thrane S. et al. (2016), see above. Briefly, the 96-well plates (Nunc MaxiSorp) were coated with 0.1 µg recombinant [M3]VAR2CSA or [HM] VAR2CSA, or [M3]HER2 or [HM]HER2 per well. Serum IgG endpoint titers were calculated on all measured days and the fold-increase in titers was determined. Arbitrary cut-off was determined by "Average[PBS]+(3*Standard Deviation [PBS])" for all plates. The statistical analysis was performed by a non-parametric, two-tailed, Mann-Whitney Rank Sum Test, with statistical significance being defined at threshold $P<0.05$.

Binding of Parasite-Infected Erythrocytes to CSA

Evaluating the antibodies ability to inhibit binding of IEs to CSA was done as previously described in Nielsen M. A. et al. (2007), *Experimental Parasitology* 117, 1-8 (2007). Briefly, mouse serum was diluted 1:20 or 1:60 in a total volume of 120 µl in 96 well Falcon plates coated with 2 µg/ml CSPG. Serum pools for each group and parasites (2×105) labeled with tritium were added simultaneously to the wells and incubated for 2 hours. Hereafter the plate was washed and the remaining cells were harvested on a filter plate and counting of adhering IE was determined by liquid scintillation counting on a Topcount NXT (Perkin-Elmer).

Human Monocyte-Derived DC Generation and Culture

DCs were generated from peripheral blood mononuclear cells (PBMCs), isolated by Ficoll-Hypaque density gradient centrifugation from buffy coats collected from anonymous healthy blood donors. Written informed consent was obtained from blood donors at the Department of Clinical Immunology, University Hospital Rigshospitalet, Copenhagen and used without the possibility to identify case specific information: The ethical committee, Region H, Capital Region of Denmark, approved the use of these buffy coats for research that was carried out in accordance with the approved guidelines. Subsequently, CD14+ monocytes were isolated from PBMCs by positive selection using magnetic beads (Miltenyi Biotec, Germany), according to the manufacturer's instructions. Monocytes were cultured at 37° C. in 5% $CO_2$ in media supplemented with 10% fetal bovine serum (FBS, Gibco) GM-CSF and IL-4 (50 ng/ml both, PeproTech) for 7 days to generate im-DC and m-DC, as previously described in Nastasi, C. et al. (2015), *Scientific Reports* 5, 1-10, and Nastasi, C. et al. (2017), *Scientific Reports* 7, 1-10. The latter was produced by stimulation with lipopolysaccharide (LPS) 2.5-100 ng/ml range, as needed, *E. coli* 055:B5, Sigma-Aldrich) for the last 24 h with and without isolated proteins.

Pulse Chase Study of Monocyte Derived DC Uptake with [M3] and [HM] Glycoforms of ID1-ID2a 10 ug of FITC-labeled ID1-ID2a with different glycosylation was added to the dendritic cell culture in 1 ml. After 2 minutes and 60 minutes, respectively, samples were taken and divided in two for the "unstripped" and "stripped".

Both were washed with ice-cold buffer (1% FBS, 0.01% sodium azide, PBS), followed by three rapid washed with ice cold acid stripping-buffer (RPMI, 0.2% FBS, pH 3.5), see Li N et al. (2008) *Methods in molecular biology* (Clifton, N.J.) 457, 305-17 (2008). At the end both were re-suspended in PBS and 7-AAD 7-AAD (BD Pharmigen) was added before acquisition at the flow cytometer to exclude dead cells.

Flow Cytometry

Cells were stained at 4° C. for 30 min in FACS buffer (1% BSA, 0.01% sodium azide, PBS), washed, and re-suspended in the same buffer. Isotype-matched antibodies were used to define and exclude the background staining and 7-AAD (BD Pharmigen) to exclude dead cells. DC analysis was conducted with anti-human HLA-pan class I (clone W6/32), HLA-DR (clone L243), anti-human CD83 (clone HB15e), CD86 (clone 2331 FUN1), CD40 (clone 5C3), CD80 (clone L307.4), all purchased at BD Bioscience.

All samples were acquired by LSRFortessa™ (BD Bioscience) at the CFFC (Core Facility for Flow Cytometry, Faculty of Health and Medical Sciences, University of Copenhagen). All data analyses were performed with FlowJo v7.0 (Treestar, Ashland, OR).

Fixation, Staining and Microscopy of Dendritic Cells

Immediately upon sampling the cells were spun down at 400×G for 5 minutes and re-suspended in 200 µl 2% Paraformaldehyde (Alfa Aesar cat. No. J61899 diluted to 2% in PBS (cat no)) and stored at 4° C. for 6 days. Hereafter, all steps were carried out at room temperature. Approximately $0.5×10^6$ cells were spun down at 600×G for 5 minutes and washed in PBS. Hereafter "spun" refers to 600×G for 4 minutes. The cell membrane was permeabilized in buffer BB+0.2% Triton for 30 minutes. Blocking of unspecific antibody binding was done in BB+10% normal donkey serum (NDS). The Alexa Fluor® 647 anti-human CD107a (LAMP-1) Antibody (cat. No. 328611, BioLegend) was diluted 1:20 in BB+1% NDS and the cells were re-suspended in 50 µl and incubated for 25 minutes. Hereafter the cells were stained with Dapi, diluted 1:1000 in PBS for 5 min and washed twice in PBS. After the final wash the cells were re-suspended in 100 ul PBS and 30 µl were mounted directly on a glass slide (cat. No. 631-1558, VWR), covered with Menzel-Gläser cover slips and sealed with transparent nail polish. The slides were stored at 4° C. until microscopy.

All microscopy was carried out on a laser scanning confocal microscope (Zeiss LSM 710) with a Plan-Apochromat objective with a 63× magnification and a 1.4 Numerical Aperture (Contrast DIC III, working distance 0.19 mm). The images were acquired using ZEM software on the 4×zoom, max speed (14) and 380×380 in a bidirectional manner.

Results

Analysis of N-Linked Glycans on ID1-ID2a and HER2 Expressed in WT-S2 and in Glyco-Modified S2 Cells: S2-Δα-Man-Ia It was the intention to produce wild-type (WT) insect glycosylated ID1-ID2a and HER2, as well as a highly mannosilated version of each. Both constructs were designed to allow VLP coupling via SPyTag/SpyCatcher covalent interactions. ID1-ID2a was designed as a construct that carried a N-terminal SpyTag and HER2 was designed with a N-terminal SpyCatcher. Both constructs were expressed stably from polyclonal wild-type cells (S2-WT), as well as in a polyclonal α-mannosidase-I knock-out strain (S2-Δα-Man-Ia, cf. Example 1) and purified. The N-linked glycans were cleaved off from purified glycoprotein and analyzed on LC-MS, see FIG. 7: Released glycans from WT were called [M3] and glyco-engineered high-mannose glycans were called [HM]. Purified protein is henceforth referred to as [M3]ID1-ID2a, [HM]ID1-ID2a, [M3]HER2, and [HM]HER2 respectively. On [M3]ID1-ID2a we found mostly F(6)M3, which composed 69% of the total glycan pool. We also found a small amount of M3 and M5(7%). Furthermore, there was below 5% of each of M4, A1, M6-M9. [M3]HER2 showed >84% F(6)M3 and <5% of M3 and high-mannoses. On the glyco-modified version of both antigens the glycan profile had shifted. On ID1-ID2a expressed in Δα-Man-Ia we found that F(6)M3 decreased to 17%, while the levels of high-mannose structures such as M6, M7, M8, and M9 had increased to 10, 18, 41, and 7% respectively (combined representing 76% high-mannose). The glycan pattern of HER2 shifted significantly as well, and we saw <23% F(6)M3, and >20,% 24%, and 27% of M6, M7, and M8 respectively (combined representing 71% high-mannose) on [HM]HER2.

These glycan analyses confirm that ID1-ID2a and HER2 1) are glycosylated predominantly as pauci-mannose in WT S2 cells and 2) that the glycosylation in S2 cells can be genetically engineered to consist of predominantly higher-mannose structures.

Glycan Dependent Anti-HER2 and Anti-ID1-ID2a Specific Antibody Titers in Mouse Model Primary investigation of the immunological differences in [M3] and [HM] encompassed immunizations of female BALB/c mice. [M3]HER2 and [HM]HER2 were coupled to VLPs, formulated with AddaVax and used for immunizing 4 female BALB/c mice intramuscularly. For ID1-ID2a 6 female BALB/c mice were immunized intramuscularly with either antigen formulated with AddaVax or coupled to VLPs (no AddaVax). All groups were immunized on day 0, 21, and 42, and serum samples for antibody measurements were taken on day 14, 35, and 56. Serum from day 14, 35 and 56 were analyzed by ELISA for total IgG (HER2, in FIG. 8, ID1-ID2a in FIG. 9). Based on the statistical analysis of the antibody levels there is no statistically significant difference between [M3]HER2 and [HM]HER2, neither on Day 14, 35, or 56, see FIG. 8.

To account for any glycan-related differences all ELISAs were carried out on plates coated with either [M3]ID1-ID2a or [HM]ID1-ID2a. As seen in FIG. 9, there is a statistically significant difference between [M3] and [HM] in the day 14 samples. Interestingly, when ELISA plates were coated with [M3]ID1-ID2a the antibody titer for [M3]ID1-ID2a is higher, and conversely, when the ELISA plates were coated with [HM]ID1-ID2a, the [HM]ID1-ID2a antibody titer is higher. For Day 35 bleeds there seems to be an effect using the VLPs as adjuvant, where, on HM coated plates, the [HM]ID1-ID2a gives a higher response. This could indicate that the mice also raised glycan-specific antibodies. However, the effect disappeared on the Day 56 bleed.

The statistical analysis was done with a cut-off calculated by Average[PBS]+(3*Standard deviation[PBS]) and the end-point titer was determined as the highest titer above this OD. We also analyzed the data with a higher cut-off calculated by (3*Average[PBS])+(3*Standard deviation[PBS]). Under these conditions the data did not show any statistically significant differences, suggesting that even though we see minor differences with another cut-off point, the conclusion is that total IgG level is not altered by [HM]ID1-ID2a compared with [M3]ID1-ID2a in BALB/c mice.

In order to analyze whether the antibodies from different glycan-versions elicited different antibodies with different functionality it was therefore investigated whether they were able to block parasite infected erythrocytes (IEs) to CSA.

Enhanced Prevention of Parasite Binding to CSA from Sera from ID1-ID2a Carrying High-Mannose Compared with Pauci-Mannose Even though the level of produced antibodies from mice immunized with either [M3]ID1-ID2a or [HM]ID1-ID2a were equal, their ability to prevent IEs from binding to CSA, which would simulate binding to placental cells, was tested. Testing how efficient the antibodies in serum were at preventing binding of parasite-infected erythrocytes to Condroitin sulfate A (CSA) revealed an interesting trend. The antibodies were analyzed by an inhibition assay, where CSA-coated wells of 96 well FACS plates were exposed to parasite IEs and diluted serum simultaneously. After incubation, the unbound IEs were counted.

Results are shown in FIG. 10 where the mean percentage of binding is shown relative to binding in wells without inhibitor.

According to previous parasite binding inhibition assays (Nielsen, M A et al. (2007), *Experimental Parasitology* 117, 1-8; Nielsen, M A et al. (2015), *PLoS ONE* 10, 1-12;

Nielsen, M A et al. (2009), *Infection and immunity* 77, 2482-7; and Salanti, A et al. (2010), *Malaria Journal* 9, 1-9) serum diluted 1:10 was used for comparison between antigen variants. 1:20 and 1:60 dilutions were used to achieve discrimination between the two glycoforms and it was found that at the 1:20 dilution [HM] on soluble ID1-ID2a elicits significantly better antibodies than [M3]ID1-DI2a. For the VLP-coupled antigens, there is no statistically significant difference. However, both samples are relatively low, so this is probably a titration issue. Looking at the 1:60 dilution, there is a significant difference for both soluble antigen and VLP-coupled antigen, and in both cases the [HM] eliciting antibodies that are significantly better at preventing binding of IE to CSA. Interestingly, it seems that the VLP-coupled antigen generally elicits antibodies with higher functionality than in presence of AddaVax.

Even though this significant difference in functionality offers great potential for an optimized vaccine as is, it was decided to conduct in vitro assays with human monocyte derived dendritic cells (mo-DCs) in order to understand the mechanistic effects behind this difference in functionality.

Qualitative Investigations of Fluorescently Labeled ID1-ID2a in mo-DC

To test whether an increased level of mannoses influenced the binding rate to DCs, which carry a specific mannose receptor CD206, [M3]ID1-ID2a and [HM]ID1-ID2a were labelled with Fluorescein (FITC) (488 nm) (not coupled to a VLP). Hereafter, activated mo-DCs were exposed to FITC-labeled ID1-ID2a and measured the fluorescence intensities by flow cytometry. FITC-labeled [M3]ID1-ID2a and [HM]ID1-ID2a were incubated with activated mo-DCs from two donors. Mean fluorescence intensities (MFIs) of activated mo-DCs was investigated after 2 minutes of pulsing and compared the two glycosylated constructs.

Results are shown in FIG. 11: MFI from the [HM]ID1-ID2a pulsed mo-DCs was lower than for the [M3]ID1-ID2a. This indicates that DCs recognize and bind ID1-ID2a with [M3] mannose residues faster than [HM] glycans. This does, however not explain the increase functionality of [HM]ID1-ID2a antibodies.

Further, it was investigated whether there was a difference in uptake path and localization of the labeled antigen depending on mannosylation level. LPS-activated mo-DCs were exposed to FITC-labeled [M3]ID1-ID2a and [HM]ID1-ID2a for 60 minutes and were visualized by confocal microscope. The nucleus of the mo-DCs was stained with DAPI and the lysosome with an anti-human CD107a, which recognizes the Lysosomal-Associated Membrane Protein 1 (LAMP-1 or CD107a) on the surface of the lysosome, to see if the ID1-ID2a antigen was transported to the lysosomes. No differences in transport route for the two glycoforms were found via this analysis for[M3]ID1-ID2a and [HM]ID1-ID2a. However, it appeared clearly that both proteins were taken up by the DCs and transported inside the cell.

In summary, a glycoform of the PM antigen ID1-ID2a was established, which produces significantly better functional antibodies in mice, compared with a WT PM vaccine. The level of antibodies was the same for both tested antigens, ID1-ID2a and HER2. In the in vitro mo-DC analyses we performed, we found that the [M3]ID1-ID2a has a higher binding rate to mo-DCs than [HM]ID1-ID2a.

Discussion

WT and glyco-engineered ID1-ID2a and HER2 were expressed and a significant increase in functionality of antibodies elicited by [HM]ID1-ID2a compared with [M3]ID1-ID2a was observed in mice. The effect of M3 vs. HM glycans on various DC assays was evaluated. Results showed that
1) S2 cells generally express ID1-ID2a and HER2 with F(6)M3 as the primary glycan structure (69% and 84% respectively),
2) after successful expression of ID1-DI2a and HER2 in a glyco-engineered cell line (see Example 1), both antigens were found to carry high-mannose (M5-M9) glycan structures in >75% of the total glycan pool,
3) the increased level of mannose in [HM]ID1-ID2a and [HM]HER2 does not influence total antibody levels, independent of adjuvant or adjuvant combination,
4) The [HM]ID1-ID2a elicits antibodies with higher functionality and thereby a better ability to inhibit binding of IEs to CSA compared to [M3]ID1-ID2a, irrespective of administration as soluble antigen or coupled to a VLP,
5) mo-DCs take up both [M3]ID1-ID2a and [HM]ID1-ID2a, however, binding rate of the two differs with [HM] having a lower binding rate to mo-DCs than [M3], and lastly
6) there are indications of differences in glycoform for surface marker up-regulation for [M3] and [HM] (results not shown).

Interestingly, when we compare different levels of LPS (data not shown), it appears that for 1.25, 2.5, and 5 ng of LPS most samples are lower than the control, where only LPS and not antigen/VLP was added. This suggests that even though DCs have mannose specific receptors, either the protein or the glycans have a dampening effect on the activation of DCs.

In particular, the abilities of sera from [M3] and [HM] pools to inhibit binding of IEs to CSA differed significantly. The antibodies in sera from mice immunized with [HM] ID1-ID2a were superior in preventing binding to CSA compared to [M3]ID1-ID2a. This could be due to the different immune pathways that the two glycans activate. The MR on DCs has higher binding affinity towards [M3] than [HM]. It is likely that the [M3]ID1-ID2a binds to activated DCs and is presented by MHC molecules on the DC surface to a larger extent than [HM]ID1-ID2a. In contrast to this, MBL has been shown to bind with stronger affinity to high-mannose structures in vitro. Binding of high-mannose structures to MBL activates the lectin pathway in the complement cascade, subsequently initiating CR2/C3d reaction with naïve B cells and activation of these. The difference shown here in antibody functionality between [M3] and [HM] on ID1-ID2a could potentially be due to these different polarizations of the immune response.

In conclusion, two glycomodified antigens were expressed and purified the effects of glycomodification to WT glycosylation in vivo in mice and in vitro in mo-DCs were investigated. The total antibody levels in immunized mice did not vary between glycan-groups, neither for ID1-ID2a or HER2. Remarkably, when the antibodies' functionality was scrutinized, it was found that sera from [HM]ID1-ID2a was significantly better at inhibiting binding of IEs to CSA than [M3]ID1-ID2a, suggesting an enhanced effect of high-mannose vs. pauci-mannose in the PM vaccine. These findings will benefit the vaccine field, especially in regards to efficacy of glycosylated recombinant antigens or therapeutics.

Example 3

Fucosylation in *Drosophila* S2 Cells and Test of Immunological Effects of Glyco-Modified Placental Malaria Vaccine in Mice

INTRODUCTION

It was decided to increase efficacy of a placental malaria vaccine antigen, VAR2CSA, expressed in *Drosophila* S2 cells. The strategy to achieve this was based on enhancing vaccine antigen immunogenicity by modifying its glycosylation pattern, partly based on the findings in Example 2. The enhancing effect was achieved by adding core α1,3-linked fucose to the pauci-mannose glycan structure and subsequently analyzing the antibody titers in mice and the functionality of the induced antibodies. In addition, the fucosylation properties of S2 cells in general was investigated.

EXPERIMENTAL

Plasmid Constructs

Human erythropoietin (hEPO, GenBank: ACJ06770.1) was synthesized with an N-terminal BiP signal (MKLCIL-LAVV AFVGLSLG, SEQ ID NO:22) and a C-terminal purification StrepII-tag (WSHPQFEKGG GSGGGSGGSS AWSHPQFEK, SEQ ID NO:23). This gene sequence was flanked by EcoRI and NotI restriction sites to allow easy cloning into the multiple cloning site of pExpreS$^2$-BLAST (ExpreS$^2$ion Biotechnologies, Denmark). The final construct was named hEPO, pExpreS$^2$-BLAST.

Ebola Glycoprotein 1 V4 (GenBank: AHL68679.1) was likewise synthesized with an N-terminal BiP secretion signal, a C-terminal purification tag (EPEA, SEQ ID NO:24) and flanked by EcoRI and NotI restriction sites. The synthetic construct was inserted into pExpreS$^2$-BLAST and the final construct called Ebola GP1, pExpreS$^2$-BLAST.

The *Arabidopsis thaliana* fut11 gene was received from Copenhagen Center for Glycomics at the Department of Cellular and Molecular Medicine at University of Copenhagen in the EPB69 vector. The gene was flanked by EcoRI and NotI restriction sites and inserted in both pExpreS$^2$-BLAST and pExpreS2-2, resulting in the final constructs: fut11, pExpreS$^2$-BLAST and fut11, pExpreS$^2$-2.

S2 Cell Culture

The ExpreS$^2$ *Drosophila* S2 (S2-WT) cell line was used for all cell work (ExpreS$^2$ion Biotechnologies, Denmark). The cells were maintained and transfected as described previously in Hjerrild K A et al. (2016), cf. Example 1. Briefly, stable transfections were carried out in 2×10$^6$ c/ml in 5 ml EX-CELL 420 serum-free medium in a 25 ml tissue-culture flask (T25) by addition of 50 µl ExpreS$^2$ Insect-TRx5 transfection reagent and 12.5 µg purified plasmid DNA. A stable cell line was selected for by adding either 100 µg/ml blasticidin (InvivoGen) or 4000 µg/ml Geneticin (InvivoGen) and maintaining selection for three weeks. Transient transfections were carried out in a larger scale in shake flasks. Cells were passaged by centrifugation on day 0 to 8×10$^6$ c/ml in 300 ml EX-CELL 420. On day 1 the cells were split by centrifugation to 8×10$^6$ c/ml and transfected by addition of 100 µl ExpreS$^2$ Insect-TRx5 (ExpreS$^2$ion Biotechnologies, Hersholm) and 20 µg of plasmid DNA. S2-fut11 was constructed by stably transfecting fut11, pExpreS$^2$-2 into S2-WT. ID1-ID2a was transfected stably into S2-WT and termed S2-VAR2CSA herein. Also, the cell line S2-VAR2CSA-fut11 was constructed by stably transfecting fut11, pExpreS2-2 into the S2-VAR2CSA.

In Example 1 was provided an S2 cell line where FucT6 is knocked outs (M:ΔFucT6 in Example 1), and ΔFucT6-fut11 was constructed by stably transfecting fut11, pExpreS$^2$-BLAST into ΔFucT6. Below in the following table is provided an overview of the cell lines used in this example:

| Cell line name | Characteristics |
| --- | --- |
| S2-WT | Wild type S2 cells |
| S2-fut11 | S2-WT with stably transfected fut11 gene |
| ΔFucT6 | S2-WT with knocked out α1,6-fucosyltransferase |
| ΔFucT6-fut11 | ΔFucT6 with stably transfected fut11 gene |
| S2-VAR2CSA | Monoclonal cell line used for GMP production expressing the placental malaria antigen, VAR2CAS (ID1-ID2a) |
| S2-VAR2CSA-fut11 | VAR2CSA with stably transfected fut11 gene |

List of cell lines used in this example.

Expression and Purification of Recombinant hEPO, Ebola GP1, and VAR2CSA

Human EPO and Ebola GP1 were transfected transiently into S2-WT, S2-fut11, ΔFucT6, and ΔFucT6-fut11 cell lines. The supernatants were harvested and filtered through a 0.22 µm filter. For purifying hEPO 1:300 BioLock (iba, Göttingen, Germany) was added prior to up-concentration (1:4) and buffer exchanging (1:4) into W buffer (10 mM tris (hydroxylme-thyl)aminomethane, 15 mM NaCl, 0.1 ml EDTA, pH 8). The hEPO was captured on a Strep-Tactin® XT Superflow column and eluted by BXT buffer (iba, Göttingen, Germany). Ebola GP1 supernatant was up-concentrated (1:3) and buffer exchanged (1:4) (20 mM TRIS, 100 mM NaCl, pH 7.3) on a tangential flow filtration device (TFF). Ebola was captured on a 1 ml CaptureSelect™ C-tag affinity matrix (ThermoFisher Scientific, Waltham, MA, USA) and eluted in 10 mM TRIS, 100 mM NaCl, 1M $MgCl_2$, pH 7.3. VAR2CSA was purified as described in Example 1. Briefly, supernatant was added to 10 mM ethylenediaminetetraacetic acid (EDTA), up-concentrated 1:4 and buffer exchanged into 20 mM Sodium Phosphate buffer, 60 mM NaCl, and 5 mM EDTA, pH 6.6 and ion exchanged on a 1 ml HiTrap SP Sepharose FF column (GE Healthcare, Brøndbyvester, Denmark). VAR2CSA was eluted stepwise and then polished on a 1 ml HiTrap Capto Adhere column.

Isolation of N-Glycans

Purified protein was up-concentrated, desalted and buffer changed to 50 mM ammonium bicarbonate (VWR) using Milipore™ 3 kD Amicon™ Ultra-0.5 Centrifugal Filters (Merck). RapiGest SF buffer (Waters) in ammonium bicarbonate was added to proteins expected to carry α1,3-fucose to a final concentration of 0.05%. The protein was reduced in 5 mM DL-Dithiothreitol at 60° C. for 40 min and alkalized in 10 mM Iodoacetamide in dark at room temperature for one hour. Trypsin digestion was carried out at 25° C. for 8 hours and glycopeptides were eluted from Sep-Pak® (Waters) with 60% Acetonitrile and dried in SpeedVac and dissolved in 50 mM citrate-phosphate buffer pH 5 with 0.02% sodium azide. Glycans from all proteins were isolated by collecting flow-through and 500 µl 0.1% trofluoroacetic acid passed through a SepPak® column.

N-Glycan Analysis Using MALDI-TOF and Capillary Electrophoresis

Glycans for Capillary Electrophoresis were labelled using GlycanAssure™ APTS kit (Applied Biosystems) and analysed on a 3500xL Genetic Analyzer (Applied Biosystems) with 1% GeneScan™ 600 LIZ™ (Thermofisher) as size standard. Glycans for MALDI-TOF MS (Bruker Autoflex Speed) were permethylated by incubation with 18 mg powdered NaOH, 150 µl dimethylsulfoxide (DMSO) with 0.1% miliQ $H_2O$ and 50 µl iodomethane for 1 hour at room temperature with vigorous shake. Salt was removed by washing glycans with ice-cold mQ in chloroform. Chloroform was dried in I nitrogen trap and the glycans were dissolved in 50% methanol before spotted onto polished steel target in a 1:2 ratio with HCCA matrix in saturated solution with 70% acetonitrile, 0.1% formic acid and 2.5% NaCl. Samples were shot in reflector-positive mode calibrated to spectrum 700-3500 with 8000 shots using a nitrogen laser.

Mouse Immunizations

All immunizations contained less than 5 EU/ml. Nine-week old, female BALB/c mice (Taconic, Denmark) were immunized intramuscularly with a 30 µl vaccine (corresponding of a 5 µg of VAR2CSA per mouse per immunization in both groups) on days 0, 21, and 42. Immune serum was collected on days 14, 35, and 46 and frozen at −20° C. until use. AddaVax (15 µl AddaVax+15 µl antigen) or 9 µg MPLA per mouse/immunization both from InvivoGen (Toulouse, France) were used as adjuvants. For the mouse immunizations we used purified protein from S2-VAR2CSA-fut11 and for control, we used [M3] VAR2CSA (described as [M3]ID1-ID2a in Example 2).

Antibody Response measured by standard ELISA

Measurements of serum immunoglobulin (IgG and IgE) levels were performed by standard enzyme-linked immunosorbent assay (ELISA): Briefly, 96-well plates (Nunc MaxiSorp) were coated with 0.1 µg recombinant VAR2CSA per well. Mice sera were used as primary antibody and as secondary antibody we used Goat anti-mouse, HRP conjugated antibody (cat no. A16072 and PA1-84764, Life technologies, for total IgG and IgE respectively). Serum Ig endpoint titers on all measured days and the fold-increase in titers were calculated. The statistical analysis was performed by a non-parametric, two-tailed, Mann-Whitney Rank Sum Test, with statistical significance being defined at threshold $P<0.05$.

Inhibition of IE Binding to CSA by Glyco-Dependent Antibodies

Evaluating the antibodies' ability to inhibit binding of IEs to CSA was done as described above. Briefly, dilutions of 1:20 or 1:60 of the mouse serum was done in 96 well Falcon plates to a in a total volume of 120 µl. The wells were coated with 2 µg/ml CSPG. Serum pools for each group was added together with parasites ($2\times10^5$) labeled with tritium to the wells simultaneously and incubated for 2 hours. Hereafter, the plate was washed and the remaining cells were harvested on a filter plate. The counting of adhering IE was determined by liquid scintillation counting on a Topcount NXT (Perkin-Elmer).

Results

MALDI-TOF Analysis of the Impact of α1,3-Fucosyltransferase Insertion in S2-WT Cells on Purified hEPO, Ebola GP1 and VAR2CSA First, the *Arabidopsis thaliana* fut11 gene, which encodes an α1,3-fucosylatransferase, was inserted stably into the S2-WT and S2-VAR2CSA genomes; the purified expression products were named S2-fut11 and S2-VAR2CSA-fut11, respectively. Subsequently, hEPO and Ebola GP1 were transiently expressed in S2-WT and S2-fut11. Furthermore, VAR2CSA was produced in S2-VAR2CSA and S2-VAR2CSA-fut11. The N-linked glycans on purified glycoprotein were analyzed by MALDI-TOF and clearly showed that the three different proteins expressed in glyco-modified cells differed markedly from the wild-type glycan composition See FIG. 12.

When produced in WT cells, hEPO carried primarily mono-fucosylated pauci-mannose (FM3), no detectable amounts of M3, and showed very few peaks of higher mannose structures. The Ebola GP1 N-linked glycans were predominantly FM3, similar to hEPO, but significant amounts of M3 were also observed and, interestingly, many peaks for higher mannose structures, ranging from M5-M9, which is also seen natively. The PM vaccine antigen VAR2CSA's N-linked glycans were primarily FM3, as well as lesser amounts of non-fucosylated M3.

When hEPO, Ebola GP1, and VAR2CSA were expressed in a fut11 expressing cell line, a shift in glycan pattern was seen for all three proteins. For hEPO there was a decrease in FM3, and marked increase in amounts of F(3)F(6)M3, while the amounts of high-mannose structures did not change, signifying a phenotypic effect of the α1,3-fucosyltransferase insertion. For Ebola GP1 expressed in S2-fut11 there was also a decrease in the level of FM3, and a marked increase in levels of F(3)F(6)M3 glycan structure. Interestingly, there was also a shift in the ratios of high-mannose glycans, with a notable increase of M6 and a decrease of M8. For the PM vaccine antigen VAR2CSA expressed in S2-VAR2CSA-fut11 there was a decrease of FM3 and a peak with similar mass as F(3)F(6)M3 appeared on the MALDI-TOF analysis.

One drawback of the MALDI-TOF method is that α1,3-linked fucose and α1,6-linked fucose have equal masses and will therefore appear as the same peak on the spectrum. Therefore, to differentiate the α1,3-linked and α1,6-linked fucose, the glycans were also analyzed by capillary electrophoresis (CE).

Capillary Electrophoresis Analysis of the Impact of and 1,3-Fucosyltransferase Insertion in S2-WT Cells on Purified hEPO, Ebola GP1 and VAR2CSA The samples were analyzed by CE to differentiate the mono-fucosylated F(3)M3 from the F(6)M3 peak. Since the α1,3-fucose and α1,6-fucose migrate differently on the electrophoresis it was possible to separate these two structures and semi-quantify them. The CE analysis gave the same overall picture as the MALDI-TOF analysis. For all three model proteins expressed with fut11 there was a shift in the glycosylation pattern towards F(3)M3 and F(3)F(6) M3, as expected. The relative percentages are listed in the following table:

| Relative [%] | M3 | F(6)M3 | F(3)M3 | F(3)F(6)M3 |
| --- | --- | --- | --- | --- |
| hEPO in S2-WT | 2 | 94 | 4 | 0 |
| hEPO S2-fut11 | 4 | 4 | 29 | 63 |
| Ebola in S2-WT | 19 | 78 | 1 | 2 |
| Ebola S2-fut11 | 9 | 5 | 49 | 37 |
| VAR2CSA from S2-VAR2CSA | 26 | 72 | 2 | 0 |
| VAR2CSA from S2-VAR2CSA-fut11 | 5 | 2 | 64 | 29 |

The table shows relative percentages of M3, F(6)M3, F(3)M3, and F(3)F(6)M3 by Capillary Electrophoresis (CE) on hEPO, Ebola GP1, VAR2CSA expressed in S2-WT and S2-fut11. Glycans are annotated based on the pattern observed on MALDI-TOF. The CE percentages are not mass confirmed. Full glycan profile can be seen on MALDI-TOF data in FIG. 12.

This means that S2 cells are capable of expressing α1,3-fucose when the fut11 gene is overexpressed. For VAR2CSA there was a shift in M3 levels from 26% to 5%, and a shift in F(6)M3 from 72% to 2%, and most importantly close to 90% of total glycans contained α1,3-fucose, as either F(3) M3 or F(3)F(6)M3.

Capillary Electrophoresis Analysis of the Impact of FucT6 Deletion and Insertion of 1,3-Fucosyltransferase In Example 1 was constructed an S2 cell line (ΔFucT6) that does not attach core fucose on N-linked glycans. This was achieved by knocking out the FucT6 gene (a *Drosophila* homolog to the human FUT8 gene), which encodes an α1,6-fucosyltranferase. ΔFucT6 was used to investigate the α1,3-fucosyltransferase properties of the exogenous fut11 gene. The fut11 was stably expressed in ΔFucT6 (cell line: ΔFucT6-fut11), and hEPO and Ebola GP1 were transiently expressed in both cell lines as model proteins. Glycans released from purified protein were analyzed on CE (FIG. 13). When expressed in the ΔFucT6 cell line both hEPO and Ebola GP1 had 96% M3 glycan structure. When hEPO and Ebola GP1 were expressed in ΔFucT6-fut11 there was a marked shift, as the glycosylation pattern were now 86% and 73% F(3)M3 in these cell lines, respectively.

This demonstrates that S2 cells are capable of producing α1,3-linked fucose without the presence of α1,6-fucose, when the fut11 gene is overexpressed, and that the cell line robustly fucosylates with only α1,3-fucose on these two model proteins.

Glyco-Engineered ID1-ID2a Carrying α1,3-Fucose Glycans Induced Higher Levels of Antibodies in Mice than ID1-ID2a Carrying α1,6-Fucose The immunogenicity of α1,3-linked fucose was assessed by evaluation of vaccine-induced humoral responses in mice. As control VAR2CSA carrying M3 and F(6)M3 glycans was used, obtained in Example 2, where this control is termed [M3]ID1-ID2a; in the following, the same protein is termed [M3]VAR2CSA, while VAR2CSA carrying F(3)M3 and F(3)F(6) is termed S2-VAR2CSA-fut11. The antigens were compared for two different adjuvants; MPLA (Monophosphoryl Lipid A, a synthetic form of LPS) and AddaVax (a squalene-based oil-in-water nano-emulsion). Female BALB/c mice were immunized intramuscularly on days 0, 21, and 42 and anti-VAR2CSA total IgG titers were subsequently measured by ELISA on sera obtained at days 35, and 56 (FIG. 14). It was noted that the MPLA adjuvant lacked adjuvant function in this study. However, the same trend for antibody titers by [M3]VAR2CSA compared with S2-VAR2CSA-fut11 antigens exists in both adjuvants: a statistically significant increase in antibody titers in S2-VAR2CSA-fut11 compared with [M3]VAR2CSA is observed for both second (P=0.007) and third (P=0.002) bleed.

Second, the antibody levels of Day 35 S2-VAR2CSA-fut11+AddaVax was compared with the Day 56 S2-VAR2CSA+AddaVax titer levels. This comparison showed that with two immunizations of S2-VAR2CSA-fut11, the mice reached statistically significant higher levels of antibodies than after three immunizations with [M3] VAR2CSA (P=0.01).

IgE antibodies were analyzed, but none were detected (data not shown).

Antigens Induced by Glyco-Engineered ID1-ID2a Carrying α1,3-Fucose Inhibited IE Binding to CSA Significantly Stronger than Antigens Induced by ID1-ID2a Carrying α1,6-Fucose The effect of glycans on antibody functionality was evaluated by comparing raised serum antibodies' ability to prevent binding of *P. falciparum* IEs to CSA. We analyzed both 1:20 and 1:60 dilutions to study greater nuances. This assay showed that the serum antibodies of S2-VAR2CSA-fut11 exhibited significantly improved binding inhibition of IEs to CSA, for both the 1:20 dilution (p=0.008) and the 1:60 dilution (p=0.009), compared to the [M3]VAR2CSA.

Discussion

Wild type S2 expressed hEPO was determined by both MALDI-TOF and CE analysis to have almost exclusively F(6)M3 glycosylation. However, when an α1,3-fucosylatransferase is inserted in S2-WT cells the glycosylation pattern shifts to predominantly F(3)M3 and F(3)F(6)M3, at the expense of F(6)M3. One of the main reasons for this is the substrate specificity of the α1,6-fucosyltransferase, which is unable to link fucose in the α1,6 position when an α1,3-fucose is present.

Furthermore, additional model proteins were expressed in the S2-WT, S2-fut11, ΔFucT6, and ΔFucT6-fut11 cell lines to establish the effect of specific proteins on the observed glycosylation pattern. It is clear from this comparison that there existed noteworthy protein specific variations in the glycosylation pattern between the three proteins. The most striking example of this is Ebola GP 1, where significant amounts of high-mannose glycans were detected. This further highlights the importance of taking into account not only the cell line but also the model protein when studying glycosylation. Site specific glycosylation differences, as has been shown for hEPO, is also something to keep in mind.

According to CE data of hEPO expressed in S2-WT, there is 4% F(3)M3, and the CE method also detects small amounts of apparent α1,3-fucose in other WT samples. This indicates S2 cells potentially can express small amounts of α1,3-fucose on glycans natively. Even though the *Drosophila melanogaster* fly genome encodes three different α1,3-fucosyltransferases; FucTB (UniProt: Q9VLC1), FucTC (Uniprot: P83088), and recently discovered FucTD (Gene ID: 38164), Rendić et al has previously reported that no α1,3-fucose is found in S2 cells (Rendić, D. et al. (2006), *J. Biol. Chem.* 281: 3343-3353. The small peak observed in the present example is not mass confirmed, and annotations are done solely based on the glycan pattern observed in MALDI-TOF data. Furthermore, western blot analysis using an anti-α1,3-fucose antibody provided no detectable signal.

Since plant glycans in general are thought to be allergenic in humans, the levels of IgE antibodies induce where analyzed, but no IgE (data not shown) was detected, even though BALB/c mice are capable of producing such a response.

After engineering an α1,3-fucosylating and VAR2CSA-expressing cell line, S2-VAR2CSA-fut11, VAR2CSA was produced and its fucosylation status determined. It showed close to 90% α1,3-fucosylation (both mono and di-fucosylated) and near undetectable levels of α1,6-fucose compared to around 70% α1,6-fucose for WT produced VAR2CSA. This enabled the specific study of the effect of α1,3-fucose vs. α1,6-fucose on a vaccine antigen. BALB/c mice have previously been shown to lack production of anti-plant glycan antibodies, even when vaccines produced in plants and carrying plant-glycans were injected with Freud's Adjuvant. However, in the present study, ELISA plates were coated with VAR2CSA from S2-VAR2CSA, so any anti-α1,3-fucose Abs from the vaccinated mice would not contribute to the overall higher titer level of the S2-VAR2CSA-fut11. Serum was investigated prior to immunizations for α1,3-fucose specific IgG antibodies, but none were detected (data not shown).

When comparing the antibody levels of S2-VAR2CSA-fut11 with those of [M3]VAR2CSA, a significant increase was observed, even when comparing titers after two immunizations of S2-VAR2CSA-fut11 with three immunizations of [M3]VAR2CSA when using AddaVax as adjuvant. This result strongly suggests that α1,3-fucose addition to current vaccine antigens could lead to improved vaccine responses and could potentially require fewer vaccinations to achieve clinical effect.

The increased level of antibodies is interesting, however, of far greater importance is the antibodies' ability to effectively block parasite IE binding to the placenta. Serum from mice immunized with [M3]VAR2CSA or S2-VAR2CSA-fut11 were evaluated in a binding assay in vitro, by their ability to prevent binding of *P. falciparum* IEs to CSA. Serum was diluted 1:20 and 1:60. On both dilutions a significant difference was observed, with the S2-VAR2CSA-fut11 induced antibodies being superior. However, the total level of antibodies induced from S2-VAR2CSA-fut11 compared with [M3]VAR2CSA was also significantly higher. This indicates that the α1,3-fucose carrying ID1-DI2a elicits higher levels of antibodies than primarily α1,6-fucose carrying ID1-ID2a and that this increased level of antibodies is more efficient at inhibiting binding of IEs to CSA.

CONCLUSION

It was demonstrated that S2 cells are capable of producing α1,3-linked fucose on N-linked glycans when provided with the necessary α1,3-fucosyltransferase (fut11). hEPO, Ebola GP1, and VAR2CSA were expressed and all carried the immunogenic F(3)M3 and F(3)F(6)M3 glycan structures when produced in fut11 expressing cell lines. BALB/c mice raised significantly higher levels of antibodies against VAR2CSA when it carried α1,3-linked fucose compared with S2-WT F(6)M3 glycosylation. Strikingly, also when comparing antibody titers from two immunizations of S2-VAR2CSA-fut11 with three immunizations of [M3] VAR2CSA, the S2-VAR2CSA-fut11 serum still had the highest titers. Furthermore, the increased level of antibodies seen by S2-VAR2CSA-fut11 also more efficiently inhibits binding of *P. falciparum* IEs to CSA.

These findings are relevant in the field of vaccines and it once again highlights the importance of glycans in an immune setting. The enhanced glyco-profile of the model antigen VAR2CSA proposes a lower needed vaccination dose, reduced price, and perhaps fewer vaccinations.

The invention claimed is:

1. A genetically modified non-plant eukaryotic cell comprising at least one heterologous polynucleotide sequence encoding a heterologous α1,3-fucosyltransferase, wherein the cell is capable of producing N-glycosylated polypeptide or protein carrying α1,3-fucosyl groups, and wherein the cell exhibits reduced or abolished function of at least one α1,6-fucosyltransferase encoding gene.

2. The genetically modified non-plant eukaryotic cell of claim 1, wherein the genetically modified non-plant eukaryotic cell further comprises a reduction or abolishment of expression of an α-Man-Ia gene; or
   an increase in expression of genes encoding enzymes extending glycans beyond Man3 or beyond Man5.

3. The genetically modified non-plant eukaryotic cell of claim 1, wherein the genetically modified non-plant eukaryotic cell is a mammalian cell, an insect cell, or a fungal cell.

4. The genetically modified non-plant eukaryotic cell of claim 3, wherein the mammalian cell comprises a CHO cell or a HEK cell.

5. The genetically modified non-plant eukaryotic cell of claim 3, wherein the insect cell comprises a *Drosophila melanogaster* cell.

6. The genetically modified non-plant eukaryotic cell of claim 3, wherein the insect cell comprises an S2 cell, an S3 cell, an Sf9 cell, an SF21 cell, a High5 cell, or a C6-36 cell.

7. The genetically modified non-plant eukaryotic cell of claim 3, wherein the fungal cell comprises a yeast cell.

8. The genetically modified non-plant eukaryotic cell of claim 1, wherein the heterologous α1,3-fucosyltransferase comprises a plant α1,3-fucosyltransferase.

9. The genetically modified non-plant eukaryotic cell of claim 1, wherein the at least one heterologous polynucleotide sequence comprises an *Arabidopsis thaliana* fuc11 gene.

10. The genetically modified non-plant eukaryotic cell of claim 1, which further expresses a heterologous gene encoding a non-plant polypeptide or protein comprising N-linked glycans that comprise α1,3-linked fucose, wherein at least 25% of individual protein/peptide species comprise α1,3-linked fucose, wherein the non-plant polypeptide or protein is selected from the group consisting of VAR2CA; HER2; a viral protein or polypeptide from HIV, Ebola virus, Zika virus, Chikungunya virus, Dengue virus, Hepatitis A virus, influenza virus, Polio virus, Rabies virus, Measles virus, mumps virus, rubella virus, Rotavirus virus, Smallpox virus, Chickenpox virus, Hepatitis B virus, human papillomavirus, varicella zoster virus, and Yellow fever virus; and a bacterial protein or polypeptide from *Clostridium tetanii, Corynebacterium diphtheria, Haemophilus influenzae, Bordetella pertussis, Streptococcus pneumoniae*, and *Neisseria meningitide*.

11. The genetically modified non-plant eukaryotic cell of claim 10, wherein >25% of the non-plant polypeptide or protein displays high-mannose glycans.

12. A cell line comprising the genetically modified non-plant eukaryotic cell of claim 1.

13. The cell line of claim 12, wherein the cell line is a clonal cell line.

14. A method for producing an N-glycosylated polypeptide or protein carrying α1,3-fucosyl and/or increased high-mannose groups, the method comprising culturing the genetically modified non-plant eukaryotic cell of claim 1, and subsequently, isolating the N-glycosylated polypeptide or protein from the culture mixture.

15. The method of claim 14, further comprising subjecting the N-glycosylated polypeptide or protein to further purification.

16. A method for producing an N-glycosylated polypeptide or protein carrying α1,3-fucosyl and/or increased high-mannose groups, the method comprising culturing the cell line of claim 12, and subsequently,
isolating the N-glycosylated polypeptide or protein from the culture mixture.

\* \* \* \* \*